United States Patent [19]

Noda et al.

[11] Patent Number: 5,089,269

[45] Date of Patent: Feb. 18, 1992

[54] COSMETIC CONTAINING FINE SOFT MICROCAPSULES

[75] Inventors: Akira Noda; Michihiro Yamaguchi; Masanori Aizawa; Yoshimaru Kumano, all of Yokohama, Japan

[73] Assignee: Shiseido Company Ltd., Tokyo, Japan

[21] Appl. No.: 199,977

[22] Filed: May 27, 1988

[30] Foreign Application Priority Data

| Nov. 7, 1987 | [JP] | Japan | 62-281825 |
| Mar. 18, 1988 | [JP] | Japan | 63-65318 |
| Apr. 15, 1988 | [JP] | Japan | 63-93945 |
| Apr. 15, 1988 | [JP] | Japan | 63-93947 |
| Apr. 18, 1988 | [JP] | Japan | 63-95315 |
| Apr. 18, 1988 | [JP] | Japan | 63-95316 |
| Apr. 18, 1988 | [JP] | Japan | 63-95317 |

[51] Int. Cl.$^5$ .......... A61K 7/02; A61K 7/06; A61K 9/50
[52] U.S. Cl. .......... 424/456; 424/59; 424/63; 424/70; 424/401; 424/455; 424/492; 424/502; 252/174.13; 514/844; 514/845
[58] Field of Search .......... 424/496, 497, 63, 455, 424/456, 70, 492, 401; 514/844, 846, 847, 944; 252/174.13

[56] References Cited

U.S. PATENT DOCUMENTS

| 2,800,457 | 7/1957 | Green et al. | 428/402.2 |
| 3,779,942 | 12/1973 | Bolles | 252/174.13 |
| 3,839,220 | 10/1974 | Barchas | 521/76 |
| 3,886,084 | 5/1975 | Vassiliades | 424/492 |
| 3,993,831 | 11/1976 | Vassiliades | 424/497 |
| 4,348,378 | 9/1982 | Kosti | 424/52 |
| 4,394,287 | 7/1983 | Scarpelli | 424/70 |

FOREIGN PATENT DOCUMENTS

| 0247864 | 12/1987 | European Pat. Off. |
| 1255081 | 11/1967 | Fed. Rep. of Germany |
| 1617847 | 2/1971 | Fed. Rep. of Germany |
| 2243018 | 4/1975 | France |
| 59-07351 | 4/1984 | Japan |

OTHER PUBLICATIONS

Chemical Abstracts, vol. 88, 1978, p. 275, No. 55023g.

Primary Examiner—Thurman K. Page
Assistant Examiner—Amy L. Hulina
Attorney, Agent, or Firm—Sprung Horn Kramer & Woods

[57] ABSTRACT

A cosmetic composition on an external treatment agent containing microcapsules, with an average particle size of 0.1 to 2000 μm, enclosing a hydrophobic component, wherein the microcapsules are composed of a gelatin film swollen with water.

2 Claims, 6 Drawing Sheets

COSMETIC CONTAINING FINE SOFT MICROCAPSULES

BACKGROUND OF THE INVENTION

1. Field of the Invention

The present invention relates to an external treatment agent such as a cosmetic containing fine soft microcapsules. More specifically, it relates to an external treatment agent containing gelatin capsules enclosing a liquid and/or solid hydrophobic component or a water-in-oil type emulsion therein, in which the capsules are not broken during the preparation of external treatment agents such as cosmetics, drugs, quasi drugs, but can be broken easily without escape on the palms of the hands upon usage (i.e., the term "escape" refers to the stage wherein the capsules are rubbed through the fingers or palms without rupture when the fingers and palms of the hands are rubbed together, to uniformly mix the aqueous phase which is the base and the capsules with the fingers or palms), whereby the contents are leaked out to be mixed with the outer phase, and there is no feeling of foreign matter caused by portions of the capsule films remaining after breaking, which external treatment agents also have a good useability, and excellent luster imparting effect and skin wettability, or in which the unstable water-soluble substance and lipid-soluble substance enclosed within the capsules exhibit an excellent stability without deterioration for a long term, and have an excellent luster imparting effect and wettability of the skin, with a good useability.

The present invention further relates to a method for producing microcapsules by microencapsulating hydrophobic substances according to a complex coacervation and a simple coacervation by using a hydrophilic polymer, which comprises previously forming a coacervate and then successively adding hydrophobic substances with different properties, whereby microcapsules enclosing separate hydrophobic substances can be obtained at the same time in one step without a mutually mixing of the hydrophobic substances during production, which is extremely cost-advantageous.

2. Description of the Related Art

Generally speaking, so-called external treatment agents include cosmetics, drugs, and quasi drugs. Among the above, the cosmetics are classified into basic make-up cosmetics and hair cosmetics, depending on the location at which they act or their purpose.

The basic cosmetics include cosmetic water, emulsion, and cream, which are used for applying oily components having a good quality or a hydrophilic substance having a high humectant property with a good balance to the skin when the balance of the skin humectant mechanism in a human body is disturbed by various external conditions (wind, temperature, humidity, etc.) or inherent conditions (age, etc.). For example, a cosmetic water is a hydrophilic cosmetic having a transparent appearance, comprising a humectant component, an alcohol, and water, etc., and the emulsion and cream are cosmetics comprising an oily component and an aqueous component mixed in a suitable ratio.

As make-up cosmetics, a foundation, eyeshadow, and lipsticks, may be included. These are used for varying the skin color by the application of a color, affording a three-dimensional feeling to the skin, to emphasize the color of a part of or conceal a defect of the skin, thereby creating an attractive appearance while simultaneously conditioning the skin.

The hair cosmetics include hair tonics, hair oils, and hair creams, which are used as hair conditioners and as a nutrient for the hair.

More specifically, the common function or purpose of these cosmetics is to maintain a healthy and normal stage (homeostasis) by applying a suitable oily component and humectant component or water, in accordance with the nature of the skin or hair, to thereby assist the natural humectant mechanism of skin or hair and alleviate deterioration of the skin or hair caused by changes in external environmental conditions, including natural conditions such as temperature and humidity and artificial conditions such as defatting by washing.

For an improvement of these functions, various skin effective components such as vitamins and unsaturated fatty acids have been added in the prior art emulsion type cosmetics. As effective components, although water-soluble substances such as vitamin C, etc. and lipid-soluble substances such as vitamin A, linolenic acid, etc., are known, most of the water-soluble effective components are hydrolyzed when placed in contact with water, and thus the physiological activities thereof are lost. On the other hand, most of the lipid-soluble effective components are very susceptible to autooxidation and, after forming activated radicals through a loss of hydrogen atoms by light or heat, form peroxy radicals by an absorption of oxygen, and are decomposed or polymerized via hydroperoxide (peroxide) to thereby forming carbonyl compounds, lower aldehydes, lower fatty acids, ketones and other polymers, and thus the activities thereof are lost.

Accordingly, when formulating these effective components in cosmetics or other external agents, oxidation must be prevented. As one means of preventing oxidation, a method in which the preparation of an external agent is preformed in an inert gas atmosphere such as nitrogen, and further, during filling of the product in a vessel, the air in the space in contact with the external agent is replaced with nitrogen or carbon dioxide, can be used. But this replacement with nitrogen has little effect unless not only the oxygen in the space portion but also the dissolved oxygen in the external agent are replaced with nitrogen, and the replacement with carbon dioxide may cause an undesirable rise in the acid value of the effective components, or an objectionable odor, with a lapse of time. Such preparation and storage can be performed at as low a temperature as possible, but this is practically almost impossible if the quality is to be guaranteed. Accordingly, a stabilization of external agents, for a long term has been effected by an addition of antioxidants, but since the properties and the effective concentration of antioxidants differ in accordance with the kind of effective skin component used, a drawback has arisen in that a thorough examination and much experimentation are required before practical use, which makes the method difficult to handle.

Also, the method of enclosing water-soluble and lipid-soluble effective components within microcapsules, to separate them from water and oxygen, has been investigated. But, in the known methods, a simultaneous microcapsulation of water-soluble and lipid-soluble components has been considered impossible, and the method in which the respective components are prepared separately by microcapsulation methods entirely different from each other and thereafter mixed has been used, and therefore, the preparation must be performed at least twice, which greatly increases labor costs. Further, when microcapsules enclosing a water-soluble effective component therein are formulated in a base of a cosmetic water or cream, in which water is the medium, a problem has arisen in that the water readily passes through the inside and outside of a capsule film, whereby the contents leak into the outer phase base within a short time.

In the prior art, microcapsules comprising a gelatin wall film swollen with water and enclosing liquid oil components have been formulated as an external agent, but these required an extremely strong breaking force because of the flexible wall films and contents therein when they are to be broken by compression by rubbing the palms of the hand together upon usage. Namely, when palms of the hands were rubbed together, the microcapsules were only slid over the skin surface or embedded in the skin pores, whereby sometimes breaking did not occur, and thus the efficacy of the oil components enclosed was not exhibited.

For example, as mentioned above, a cosmetic water is prepared by solubilizing an oil component (i.e., emollient agent), a flavor, and a medicament, to obtain a transparent appearance, and an O/W type emulsion or cream is prepared as an emulsion containing a large amount of an emulsified oil component, thereby enhancing the humectant effect and the emollient effect on the skin. Namely, to enhance the emollient effect on the skin, a large amount of an oil component is formulated by solubilization or emulsification with a large amount of an emulsifier, but the emulsifiers generally used more or less irritate the skin, in spite of the surfactant ability thereof. Accordingly, from the viewpoint of safety, the amount of surfactant formulated therein is limited, and thus the amount of the oil component to be solubilized and emulsified must be limited. Namely, a problem has arisen in that the desired humectant effect or the emollient effect cannot be imparted to the skin.

As a means for solving these problems, the formulation of microcapsules enclosing an oil component in a cosmetic has been considered. For example, Japanese Unexamined Patent Publication (KOKAI) No. 61-112897 discloses a surfactant solution containing capsules having an improved dispersibility provided by an adjustment of the specific gravity. Also, Japanese Unexamined Patent Publication (KOKAI) No. 59-73510 disclosed that, by formulating capsules comprising a polymerizable polymeric film enclosing a skin emollient component, a flavor, and a drug component in a cosmetic, the feeling during use of a make-up cosmetic can be improved. But, according to trace experiments by the present inventors, "escape" of the capsules disclosed by the former specification occurred during usage, and thus the capsules cannot be easily disintegrated by compression, whereby a leakage of the enclosed contents could not be realized. On the other hand, the capsules used in the latter specification, when formulated in a cosmetic water or cream, can be disintegrated by compression only with difficulty, due to extremely fine capsule particle sizes of 1 to 100 μm, and further, even if integrated the film substance of the capsules remained, thus having the drawback of a feeling of foreign matter on the skin.

Furthermore, it is known to control the strength of the wall film by controlling the thickness of the wall film of a microcapsule or formulating a fine powder of mica and titanium into the wall film. But, in the former method of controlling the film thickness, the film must be made extremely thin so that the capsules are easily broken, and therefore, the capsules may sometimes break during the preparation of the product. Further, when microcapsules are to be prepared by the coacervation method, in which a gelatin film is formed after dispersing the oil component into water, the particle sizes of the capsules are nonuniform, and the breaking strength differs in accordance with the particle size even if the film thickness is the same, and therefore, the breaking strength must be based on both the film thickness and the particle size, and thus the preparation becomes extremely complicated. On the other hand, in the latter method of using a fine powder, the transparency of the gelatin film is impaired, depending on the kind of fine powder used, and therefore, the film cannot be applied to a product in which the color of the content is emphasized. Further, when the above coacervation method is utilized, since a fine powder is added into the outer phase, the amount precipitated together with the coacervate on the oil droplet surface is extremely small, and most of it is discarded together with the outer aqueous phase in the washing step, which is cost-disadvantageous, and even if the fine powder is contained in the wall film, the differences in breaking strength due to the size of capsule still remain as a disadvantage thereof.

Many methods for microencapsulating hydrophobic substances are known, and of these methods, the coacervation method utilizing the phase separation phenomenon of hydrophilic polymer can be practiced relatively easily if a device for emulsifying and dispersing hydrophobic substances into water is used, and finished microcapsules having dense wall films with a high coverage ratio can be produced, and thus this is an industrially useful production method.

In the prior art, when microcapsules are to be produced by the coacervation method, hydrophobic substances are dispersed or emulsified in an aqueous solution of a hydrophilic polymer to desired particle sizes, and then a hydrophilic polymer having opposite charges in the case of the complex coacervation method, or an electrolyte or a poor solvent are added in the case of the simple coacervation method, to effect microencapsulation.

Such prior art methods are useful for the microencapsulation of one kind of hydrophobic substance, but are not suitable for the microencapsulation of two or more kinds of hydrophobic substances with different properties. When microcapsules are produced by coacervation after dispersion or emulsification by successively adding hydrophobic substances into an aqueous hydrophilic polymer solution, an agglomeration or mutual coalescence of the hydrophobic substances will occur during dispersion or emulsification, and thus microcapsules of mixed hydrophobic substances are formed and microcapsules enclosing separate hydrophobic substances can not be obtained. Accordingly, when several kinds of microcapsules enclosing different hydrophobic substances are to be formulated in a product, the number of steps must correspond to the number of kinds of microcapsules, and must be repeated to produce microcapsules enclosing different hydrophobic components, and thereafter, the respective microcapsules must be uniformly mixed into the product.

Generally speaking, when producing microcapsules by coacervation, hydrophobic substances are enclosed with a water-soluble polymer, and thereafter the water-soluble polymer is hardened and made insoluble in water. Since a substance of higher reactivity such as aldehydes is used as the hardening agent, a washing operation must be carried out to completely remove excess hardening agent, e.g., by thoroughly washing the microcapsules after production with purified water. To accomplish this washing, a method in which the steps of removing the aqueous phase portion after complete separation of the microcapsules by standing and again adding the same amount of purified water are repeated, and a method in which the steps of adding the same amount of purified water after separation of the microcapsules from the aqueous phase with a filter are repeated, are known, but both require much time and labor.

Therefore, in the above method in which the same number of steps as the kinds of capsules are repeated, too much time and labor are required for preparing one product, which is extremely cost-disadvantageous.

Also, in the coacervation method, microcapsules with extremely different size or of wall films states may be formed if slight changes in conditions occur, and therefore, when formulating many kinds of microcapsules enclosing different hydrophobic substances in a product, conventionally the sizing was made with a sieve, or the uniformity was disregarded, but the cost was disadvantageously high and a product having a satisfactory appearance could not be obtained.

SUMMARY OF THE INVENTION

Accordingly, the objects of the present invention are to eliminate the above-mentioned disadvantages of the prior art and to provide an external treatment agent comprising microcapsules having a strength such that they are not broken by mixing during the preparation of cosmetics, drugs, quasi drugs but can be broken by rubbing the palms of the hands together upon usage, formulated therein, whereby the contents leak out and are thoroughly mixed with the outer phase, and thus a feeling of foreign matter caused by portions of the capsule films remaining after breaking does not occur, the external agent having a good useability and an excellent luster imparting effect and skin wettability.

Another object of the present invention is to provide an external treatment agent containing an active component with an excellent stability, which agent will not deteriorate over a long term.

A further object of the present invention is to provide a process for producing microcapsules at a low cost, in which microcapsules enclosing separate hydrophobic substances can be obtained simultaneously and in one step without a mutual mixing of the hydrophobic substances during production.

Other objects and advantages of the present invention will be apparent from the following description.

In accordance with the present invention, there are provided:

(1) A cosmetic composition comprising gelatin capsules enclosing a hydrophobic component therein in an aqueous phase containing a water-soluble polymer, a weight ratio of the hydrophobic component to gelatin being 1:10 to 100:1, the average particle size of the gelatin capsules being 100 to 1000 $\mu$m, and the viscosity of the system being 1000 or 20000 cps.

(2) A cosmetic composition comprising microcapsules with an average particle size of 50 to 1000 $\mu$m composed of a gelatin film swollen with water enclosing a hydrophobic component therein, characterized in that a mixture of a liquid oil component and a solid oil component or a semi-solid oil component is used as the hydrophobic component, and the microcapsules have a breaking strength of 10 to 300 g/cm$^2$.

(3) A water-in-oil type emulsified external agent, comprising microcapsules with particle sizes of 100 $\mu$m or less formulated therein, the microcapsules comprising a gelatin film swollen with water enclosing a hydrophobic component therein.

(4) An external agent comprising microcapsules made of a gelatin film swollen with water and having particle sizes of 0.1 to 50 $\mu$m, and enclosing a hydrophobic component therein and a polyhydric alcohol formulated as the essential components therein, the microcapsules after formulation having a breaking strength of 10 to 300 g/cm$^2$.

(5) An external agent comprising microcapsules made of a gelatin film swollen with water and having particle sizes of 50 to 100 $\mu$m, and enclosing either a liquid or a solid hydrophobic component therein and polyhydric alcohol formulated as the essential components therein, the microcapsules after formulation having a breaking strength of 10 to 300 g/cm$^2$.

(6) An external agent comprising microcapsules made of a gelatin film swollen with water and having particle sizes of 100 to 1000 $\mu$m, and enclosing either a liquid or a solid hydrophobic component therein and a polyhydric alcohol formulated as the essential components therein, the microcapsules after formulation having a breaking strength of 10 to 300 g/cm$^2$, and further, not having a water-soluble polymer formulated therein.

(7) An external agent comprising microcapsules made of a gelatin film swollen with water and a water-in-oil type emulsion enclosed therein.

(8) A method for producing microcapsules by microencapsulating hydrophobic component by the complex coacervation of hydrophilic polymers, which comprises previously obtaining a mutual mix of aqueous solutions of polymers having positive and negative opposite charges to form a complex coacervate, and then adding successively different several kinds of hydrophobic component, thereby obtaining microcapsules containing separate hydrophobic components, at the same time and in one step.

(9) A method for producing microcapsules by microencapsulating hydrophobic component by the simple coacervation of hydrophilic polymers, which comprises previously adding an electrolyte or a poor solvent for the polymer into an aqueous solution of a hydrophilic polymer to form a simple coacervate, and then successively adding several different kinds of hydrophobic component, thereby obtaining microcapsules containing separate hydrophobic components, at the same time and in one step.

BRIEF DESCRIPTION OF THE DRAWINGS

The present invention will be better understood from the description set forth below with reference to the accompanying drawings, wherein.

DESCRIPTION OF THE PREFERRED EMBODIMENTS

Figure 1:
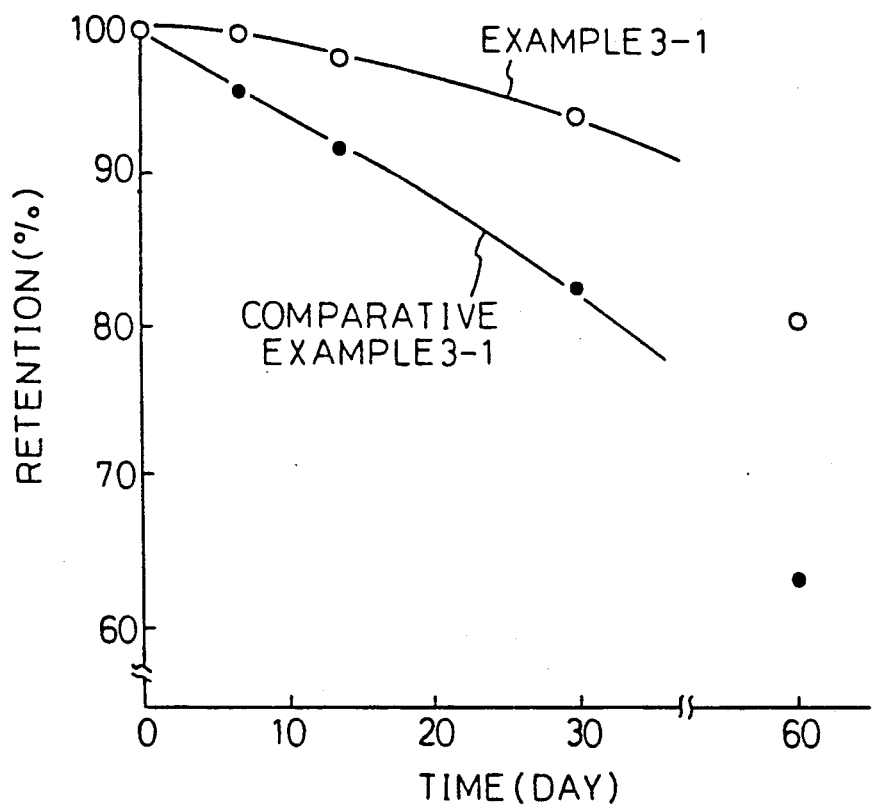
FIG. 1 is a graph showing the stability with a lapse of time of the vitamin A palmitate of Example 3-1 and Comparative Example 3-1.

According to the present invention capsules, can be readily disintegrated by compression without "escape" by rubbing with the fingers or palms of the hands when applying than to the skin, by using gelatin as the film substance for the capsule enclosing a hydrophobic component, and further, restricting the weight ratio of the hydrophobic component to gelatin within the capsules, the particle size of the capsules, and the viscosity of the outer phase including the water-soluble polymer, to within specific ranges, and thus an excellent capsule-containing cosmetic that does not produce a feeling of foreign matter due to remaining portions of the capsule can be produced.

Also, according to the present invention, by using a gelatin swollen with water as the film substance of the capsules, and varying the kind or composition of the mixture of the liquid oil component or the solid or semi-solid oil component to be enclosed, the breaking strength of the capsules can be easily controlled; i.e., if the breaking strength is limited to a certain specific range, no breaking occurs at all during preparation of the cosmetic and compression disintegration can be effected easily without "escape" of the capsules during the application onto skin and without the feeling of foreign matter caused by remaining portions of the film. Further, by formulating microcapsules having a substantially equal strength over a wide range of particle sizes, a cosmetic substantially not affected by the particle sizes of the capsules, which have a transparent wall film, can be produced.

Furthermore, according to the present invention, by enclosing lipid-soluble skin effective components in microcapsules comprising a gelatin film swollen with water and having particle sizes of 100 μm or less, and formulating the microcapsules in a water-in-oil type emulsified external agent, an excellent stability can be exhibited for a long term, to prevent deterioration thereof, and excellent specific features are obtained in that the microcapsules are not broken even under a high shear pressure during preparation of an external agent, and that the lipid-soluble effective components enclosed do not migrate to the outer oil layer by passing through the film.

Furthermore, according to the present invention, by dispersing microcapsules using a gelatin swollen with water as the film substance in a base containing a polyhydric alcohol, even with a particle size of less than 100 μm, the breaking strength of the capsules can be easily controlled by varying the kind or composition of the polyhydric alcohol, and that if the breaking strength is limited to a certain specific range, an external agent formulated with transparent microcapsules can be prepared, these microcapsules being such that no breaking occurs at all in mixing during preparation of the external agent and compression disintegration can be effected easily without an escape of capsules during application onto the skin, and without a feeling of foreign matter caused by remaining portions of the film.

Furthermore, according to the present invention, by dispersing microcapsules using a gelatin swollen with water as the film substance enclosing fluid oil components in a base containing a polyhydric alcohol, even including no water-soluble polymer with a particle size of 100 to 1000 μm, the breaking strength of the capsules can be easily controlled by varying the kind or composition of the polyhydric alcohol, and that if the breaking strength is limited to a certain specific range, an external agent formulated with transparent microcapsules can be prepared, the microcapsules being such that no breaking occurs at all in mixing during preparation of the external agent and compression disintegration can be effected easily without escape of capsules during application onto the skin and without a feeling of foreign matter caused by remaining portions of the film.

Furthermore, according to the present invention, by formulating microcapsules comprising a gelatin film swollen with water enclosing a water-in-oil type emulsion formed of an aqueous phase portion having a water-soluble skin effective component dissolved or dispersed therein and an oil phase portion having a lipid-soluble skin effective component dissolved or dispersed therein in an external agent, an excellent stability can be exhibited through an inhibition of a deterioration of the water-soluble and lipid-soluble components, and since both components can be microencapsulated simultaneously, a cumbersome operation is not required, which is cost-advantageous, and further, an entirely novel function, appearance, and useability not found in the prior art can be imparted without migration of the enclosed water-soluble effective component by passing through the film.

Furthermore, according to the present invention, extremely cost-advantageous microcapsules can be produced by successively adding hydrophobic substances with different properties after a previous formation of a coacervate, when microencapsulating hydrophobic substances according to a complex coacervation and a simple coacervation, by using a hydrophilic polymer.

Embodiment (1)

As the water-soluble polymer to be formulated in the aqueous phase of the cosmetic composition of the present invention, natural polymers, semi-synthetic polymers and synthetic polymers may be included, specific examples of which include natural polymers such as carrageenan, alginic acid, tragacanth, pectin, starch, xanthan gum, gelatin, casein agar, gum arabic, semi-synthetic polymers such as derivatives of starch, cellulose, alginic acid, and synthetic polymers such as polyvinyl alcohol, polyvinyl pyrrolidone, carboxyvinyl polymer, polyethylene glycol, sodium polyacrylate, but these are not limited in this invention, and any water-soluble polymer generally used in a cosmetic may be employed.

In the present invention, one or more kinds of the above water-soluble polymers is formulated in the aqueous phase, and the viscosity value of the aqueous phase thus obtained must be within the range of 1000 to 20000 cps in terms of the value measured by a Brookfield type rotary viscometer. If lower than 1000 cps, "escape" of the capsules from the fingers or the palms during application onto the skin will occur, and if higher than 20000 cps, the feeling during use will be markedly degraded. Here, the viscosity measuring instrument used by the present inventors is specifically a B type viscometer Model B8L produced by Tokyo Seiki Co., Ltd., and the measurement was carried out using a rotor #4 at 12 rpm.

As the method for preparing capsules of the gelatin film to be formulated in the cosmetic composition of the present invention, known methods may be used, such as the simple coacervation or the complex coacervation and other methods, but generally the complex coacervation method is employed.

Next, as the hydrophobic component to be enclosed in the above gelatin film capsule, there may be included animal and vegetable oils, hydrocarbon oils, ester oils, silicone oils, higher fatty acids, higher alcohols, waxes, vitamins, vitamin-like acting substances, various flavors. Specific examples of these may include animal and vegetable oils such as mink oil, turtle oil, safflower oil, grape seed oil, soybean oil, sesame oil corn oil, rapeseed oil, sunflower oil, cottonseed oil, avocado oil, olive oil sasanqua oil, tsubaki (camellia) oil, persic oil, castor oil, jojoba oil, peanut oil, orange oil; hydrocarbon oils such as fluid paraffin, squalane, microcrystalline wax, petrolatum, etc.; ester oils such as isopropyl myristate, isopropyl palmitate, butyl stearate, hexyl laurate, isononyl isononanate, isotridecyl notate, 2-ethylhexyl palmitate, 2-hexyldecyl laurate, 2-octyldecyl palmitate, 2-octyldodecanyl myristate, di-2-hexyldecyl azipate, di-2-ethylhexyl succinate, diisostearyl malate, 2-octyldodecanol lactate, glycerine triisostearate, diglycerine triisostearate; silicone oils such as methylpolysiloxane, methylphenylpolysiloxane, fatty acid modified polysiloxane, fatty acid alcohol modified polysiloxane, polyoxyalkylene modified polysiloxane; higher fatty acids such as myristic acid, palmitic acid, stearic acid, behenic acid, oleic acid, linoleic acid, linolenic acid, isostearic acid; higher alcohols such as cetanol, stearyl alcohol, oleyl alcohol, lanolin alcohol; waxes such as beeswax, candelilla wax, whale wax, carnauba wax; vitamins such as vitamin A, $B_2$, D, E; vitamin-like acting substances such as $\alpha$-lipoic acid, ferulic acid; sunscreening agents such as ethyl paraaminobenzoate, oxybenzone, etc.; and various natural and synthetic flavors. These however, are not limited in the present invention, and any lipid-soluble starting material generally applied to a cosmetic may be employed.

The particle size of the capsules to be applied in the present invention is 100 to 1000 $\mu$m. If the capsule particle size if smaller than 100 $\mu$m, a high wall film strength will occur and breaking of the capsules only by pressure of the fingers or palms of the hands when used as the cosmetic such as a cosmetic water or cream, can be done only with difficulty (sometimes the enclosed contents cannot be released), and if the particle size exceeds 1000 $\mu$m, "escape" of the capsule from the fingers or palms of the hands during application to the skin becomes marked.

Further, the capsules enclosing various hydrophobic components therein can be formulated in the cosmetic preferably within the range of 0.1 to 95% by weight.

The weight ratio of the hydrophobic components forming the capsules to gelatin is within the range of 1:10 to 100:1. If the weight ratio of the hydrophobic components to gelatin is greater than 1:10, the wall film of the capsules becomes too thick, "escape" of the capsules becomes marked, the capsules cannot be easily broken, and further, even if broken, portions of the wall film remain to give a feeling of foreign matter to the skin. On the other hand, if the weight ratio is greater than 100:1, the strength of the capsule film is remarkably lowered, and thus the capsules may be broken during preparation of the product, and therefore are not suitable for practical application.

The above gelatin capsule film of the present invention is amorphous per se and is transparent, and further, has a sufficient non-transmissivity relative to the contents enclosed therein.

The present invention can obtain an effect not found in the prior art, by formulating the microcapsules obtained as described above in cosmetic compositions such as cosmetic water and emulsion creams, etc.

Embodiment (2)

As the method for preparing microcapsules of gelatin film according to the present invention, known methods may be available such as simple coacervation, complex coacervation and other methods, but generally the complex coacervation method is employed.

Next, as the liquid oil component to be enclosed within the above gelatin film microcapsules, there may be included animal and vegetable oils, hydrocarbon oils, ester oils, silicone oils, higher fatty acids, higher alcohols, sunscreening agents, vitamins, vitamin-like acting substances, various flavors, but these are not limited in the present invention, and lipid-soluble starting material having a liquid appearance with a melting point lower than normal temperature (25° C.), which can be applied to cosmetics in general, may be employed.

Also, as the solid or semi-solid oil component to be enclosed in the gelatin film microcapsules in combination with the above liquid oil component, there may be included animal and vegetable oils, hydrocarbon oils, ester oils, higher fatty acids, higher alcohols, waxes, sunscreening agents, flavors, but these are not limited in the present invention, and any material which can be applied to cosmetics in general, has a melting point higher than normal temperature, and can be dissolved or dispersed in the liquid oil component to be combined therewith may be employed.

Specific examples of the liquid oil component, solid or semi-solid oil component mentioned above may include liquid oils such as avocado oil, tsubaki (camellia) oil, turtle oil, macadamia nut oil, corn oil, mink oil, olive oil, rapeseed oil, yolk oil, sesame oil, persic oil, wheat germ oil, sasanqua oil, castor oil, linseed oil, safflower oil, cottonseed oil, perilla oil, soybean oil, peanut oil, teaseed oil, kaya oil, rice bran oil, China wood oil, Japan wood oil, jojoba oil, germ oil, triglycerine glycerine trioctanoate, glycerine triisopalmitate; solid fats such as cacao butter, coconut oil, horse fat, hardened coconut oil, palm oil, tallow, sheep fat, hardened tallow, palmkernel oil, lard, cattle born fat, woodwax kernel oil, hardened oil, cattle leg fat, woodwax, hardened castor oil; waxes such as beeswax, candelilla wax, cotton wax, carnauba wax, bayberry wax, insect wax, whale wax, montan wax, rice bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol POE hydrogenated lanolin alcohol ether; hydrocarbons such as fluid paraffin, ozocerite, squalene, pristane, paraffin, ceresine, squalane, petrolatum, microcrystalline wax; synthetic esters such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 1,2-hydroxystearate, ethylene glycol di-2-ethylhexylate, dipentaerythritol fatty acid ester, N-alkylglycol monoisostearate, neopentylglycol dicaprylate, diisostearyl malate, glycerine di-2-heptylundecanoate, trimethylolpropane tri-2-ethylhexylate, trimethylolpropane triisostearate, pentaneerythritol tetra-2-ethylhexylate, glycerine tri-2-ethylhexylate, trimethylolpropane triisostearate, cetyl-2-ethylhexanoate, 2-ethylhexyl palmitate, glycerine trimyristate, tri-2-heptylundecanoic acid glycerin, castor oil fatty acid methyl ester, oleic acid oil, cetostearyl alcohol, acetoglyceride, 2-heptylundecyl palmitate, diisobutyl azipate, N-lauroyl-L-glutamate-2-octyldodecyl ester, di-2-heptylundecyl azipate, ethyl laurate, di-2-ethylhexyl sebacate, 2-hexyldecyl myristate, 2-hexyldecyl palmitate, 2-hexyldecyl azipate, diisopropyl sebacate, 2-ethylhexyl succinate, ethyl acetate, butyl acetate, amyl acetate, triethyl citrate; higher fatty acids such as lauric acid, myristic acid, palmitic acid, stearic acid, behenic (behenyl) acid, oleic acid, 12-hydroxystearic acid, undecylenic acid, thoric acid, lanolin fatty acid, isostearic acid, linoleic acid, linolenic acid, eicosapentaenic acid; straight or branched higher alcohols such as lauryl alcohol, cetyl alcohol, steryl alcohol, behenyl alcohol, myristyl alcohol, oleyl alcohol, cetostearyl alcohol, monostearyl glycerine ether (bathyl alcohol), 2-decyltetradecynol, lanolin alcohol, cholesterol, phytosterol, hexyldodecanol, isostearyl alcohol, octyldodecanol; sunscreening agents such as ethyl paraaminobenzoate, oxybenzone, etc.; and natural and synthetic flavors. Among the above, those having a melting point not higher than normal temperature are classified as liquid oil components, and those having a melting point higher than normal temperature are classified as solid or semi-solid oil components.

The proportion of the liquid oil component and the solid or semi-solid oil component to be enclosed in the gelatin film microcapsules may be such that the melting point of the mixture is slightly higher than normal temperature, namely 35° to 70° C., preferably 40° to 60° C. If the melting point is lower than 35° C., the mixture is melted to become liquid because such a temperature can be generally reached during the application and, therefore, the capsules become elastic so that the breaking of the capsules become difficult with palms. If the melting point exceeds 70° C., since it is necessary to liquefy the oil phase during preparation of the capsules, the temperature of the system must be made higher than the melting point, whereby heat denaturation of the gelatin, which is the material of the capsule films, occurs and a good wall film cannot be formed on the oil droplets, which is cost-disadvantageous.

The microcapsules of the present invention have a particle size of 50 to 1000 μm. If the capsule particle size is smaller than 50 μm, irrespective of the kind of the enclosed material, the strength of the capsules is enhanced, and thus destruction only by the pressure of the palms of the hands becomes difficult when used for a cosmetic such as a cosmetic water or cream (the enclosed material sometimes cannot be released), and if it exceeds 1000 μm, "escape" of the capsules during application onto the skin becomes marked.

Further, as the amount of the capsules of the present invention formulated in the cosmetic, a range of 0.1 to 95% by weight is preferred.

The weight ratio of the hydrophobic oil component to gelatin for forming capsules may be selected within the range of 1:10 to 100:1. If the weight ratio of the hydrophobic component and gelatin is greater than 1:10, the wall film of the capsules becomes too thick, whereby portions of the wall film remain after destruction to give a feeling of foreign matter to the skin. On the other hand, if the weight ratio is smaller than 100:1, the strength of the capsule coating is remarkably lowered, and capsule destruction may occur during preparation of the product, and thus are unsuitable for practical application.

By formulating the above oil components, the breaking strength of the microcapsules can be controlled to 2 to 2000 $g/cm^2$ in terms of the compression loading value obtained by a creepmeter, but the breaking strength of the capsules in the present invention is preferably in the range of 10 to 300 $g/cm^2$ for the formulation into cosmetics. If the breaking strength of the capsules is lower than 10 $g/cm^2$, capsule breaking may occur during preparation of the product, and if higher than 300 $g/cm^2$, breaking of capsules can be effected only with difficulty when applied onto the skin, whereby the feeling during use is be remarkably degraded. The instrument for measuring the breaking strength used by the present inventors is specifically a creepmeter Rheoner RE-3305 model (produced by Yamaden Co., Ltd.), and the measurement method was carried out by compressing the capsules laid in a dense mass on a glass flat plate with a Teflon 8 mm$\phi$ columnar rod mounted on the measuring instrument, under a load of 1 g per 1 second, and the breaking strength was determined by calculating the amount of the load upon rupture, calculated per 1 $cm^2$.

The above gelatin capsule film according to the present invention is amorphous per se and is transparent, and further, has a sufficient non-transmissivity relative to the materials enclosed therein.

The present invention has obtained an effect not found in the prior art by formulating the microcapsules obtained as described above into cosmetics such as cosmetic water, emulsions, creams, shampoos, and rinses, etc.

Embodiment 3

As the method for preparing microcapsules of gelatin film to be formulated in the external treatment agent according to the present invention, known methods may be used, such as simple coacervation, complex coacervation and other methods, but generally the complex coacervation method is employed.

Next, as the hydrophobic component to be enclosed within the above gelatin film microcapsules, there may be included the animal and vegetable oils, hydrocarbon oils, ester oils, silicone oils, higher fatty acids, higher alcohols, vitamins, vitamin-like acting substances, sunscreening agents, and various flavors mentioned above. However, these are not limited in the present invention, and any lipid-soluble starting material which can be generally applied to cosmetics, drugs, quasi drugs, etc., and is laible to be peroxidized by an induction of activated radicals by the action of light or heat may be employed.

The particle size of the capsules to be applied in the present invention is 100 μm or less. If the capsule particle size is larger than 100 μm, the capsules are broken by a vigorous shearing force occurring during preparation of the water-in-oil type emulsion, whereby the lipid-soluble effective components are liable to leak into the oil phase, which is the continuous phase and susceptible to autooxidation, and when required to be broken by compression during usage of the product, an extremely strong force is required due to a flexible wall film and contents, or even if broken, a feeling of foreign matter due to remaining portions of the capsule film occurs, and thus a satisfactory product from the point of useability cannot be obtained.

Further, the capsules enclosing various hydrophobic components therein are formulated in the cosmetic composition preferably within the range of 0.1 to 95% by weight.

The weight ratio of the hydrophobic components forming the capsules to gelatin is selected within the range of 1:10 to 50:1. If the weight ratio of the hydrophobic components and gelatin is greater than 1:10, the wall film of the capsules becomes too thick, whereby the capsules can be broken with difficulty during application onto the skin. On the other hand, if the weight ratio is greater than 50:1, the strength of the capsule film is remarkably lowered, and the capsules may be broken during preparation of the product, and therefore, they are not suitable for practical application.

As the method for preparing the water-in-oil type emulsified external treatment agent of the present invention, any method generally employed may be used, including, for example, the simple emulsification method by high shearing force, the amino acid gel emulsification method utilizing the salt-out action of amino acid relative to the activating agent, and the emulsification method utilizing the gelling ability in oil of organophilic clay mineral.

The water-in-oil type emulsion external treatment agent of the present invention is an external treatment agent used for cosmetics, drugs, quasi drugs, etc., and has extremely excellent use characteristics in that a strong force is not needed when it is broken by compression during usage, and that there is no feeling of foreign matter due to remaining portions of the capsule film. Therefore, it is preferably used particularly for cosmetics having characteristics which are emphasized. For example, by formulating microcapsules with particle sizes of 100 μm or less having lipid-soluble effective components endosed therein in basic cosmetics such as an emulsion or cream or in make-up cosmetics such as a foundation or lipsticks, a water-in-oil type emulsified cosmetic imparting effects not found in the prior art can be obtained.

The above gelatin capsule film of the present invention is amorphous per se and is transparent, and further has a sufficient non-transmissivity relative to the contents enclosed therein.

Embodiment (4)

As the polyhydric alcohol to be formulated in the external treatment agent of the present invention, any starting material generally used for cosmetics, drugs, quasi drugs, etc., may be employed, such as diethylene glycol monoethyl ether, polyethylene glycol, propylene glycol, polypropylene glycol, 1,3-butylene glycol, glycerine, polyglycerine, pentaerythritol, sorbitol, glucose, sucrose, xylitose, and mannitol.

The amount of the polyhydric alcohol according to the present invention formulated in the external treatment agent is preferably within the range of 0.1 to 98% by weight.

As the method for preparing microcapsules of gelatin film according to the present invention, known methods may be used, such as simple coacervation, complex coacervation and other methods, but generally the complex coacervation method is employed.

As the hydrophobic substance to be enclosed within the microcapsules according to the present invention, there may be included the animal and vegetable oils, hydrocarbon oils, ester oils, silicone oils, higher fatty acids, higher alcohols, vitamins, vitamin-like acting substances, sunscreening agents and various flavors mentioned above. However, these are not limited in the present invention, and any lipid-soluble starting material which can be generally applied to cosmetics, drugs, quasi drugs, etc., may be employed.

The particle size of the microcapsules according to the present invention is 0.1 to 50 μm. Capsules with particle size smaller than 0.1 μm are not preferable, because they are extremely difficult to produce.

Further, the amount of the capsules according to the present invention is preferably within the range of 0.1 to 95% by weight.

The weight ratio of the hydrophobic substance forming the capsules to gelatin film is within the range of 1:0.01 to 1:10. If the weight ratio of the hydrophobic substance and gelatin is smaller than 1:0.01, the strength of the capsule coating is remarkably lowered, whereby capsule breaking may occur during preparation of the product. On the other hand, if the weight ratio is greater than 1:10, due to an increased thickness of the wall film in the capsules, the wall film may sometimes remain after breaking to give a feeling of foreign matter to the skin.

By permitting the microcapsules to be co-present with the above polyhydric alcohol, the breaking strength of the microcapsules can be controlled to 2 to 2500 g/cm$^2$ in terms of a compression loading value obtained by a creepmeter, but the breaking strength of the capsules in the present invention is preferably in the range of 10 to 300 g/cm$^2$ for formulation into the external agent. If the breaking strength of the capsules is lower than 10 g/cm$^2$, capsule destruction may occur during preparation of the product, and if higher than 300 g/cm$^2$, destruction of capsules can be effected only with difficulty when applied onto the skin, whereby the feeling during use will be remarkably degraded. The instrument for measuring breaking strength used by the present inventors is specifically a creepmeter Rheoner RE-3305 model (produced by Kabushiki Kaisha Sanden), and the measurement method was carried out by compressing the capsules laid in a dense mass on a glass flat plate with a Teflon 8 mmφ columnar rod mounted on the measuring instrument under a load of 1 g per 1 second, and the breaking strength was determined by calculating the amount of the load upon rupture, calculated per 1 cm$^2$.

The above gelatin capsule film according to the present invention is amorphous per se and is transparent, and further has a sufficient non-transmissivity relative to the materials enclosed therein.

The external treatment agent of the present invention is an external agent used for cosmetics, drugs, quasi drugs, etc., and has extremely excellent use characteristics in that a strong force is not needed when it is to be broken by compression during usage, and that there is no feeling of foreign matter due to remaining portions of the capsule film. Therefore, it is preferably used particularly for cosmetics having characteristics which are emphasized. For example, by formulating microcapsules with particle sizes of 0.1 to 50 μm having hydrophobic components enclosed therein in cosmetics such as cosmetic water, emulsions, creams, shampoos, rinses, etc., a cosmetic which can impart effects not found in the prior art can be obtained.

Embodiment (5)

As the polyhydric alcohol to be formulated in the external agent of the present invention, any starting material generally used for cosmetics, drugs, quasi drugs, etc., mentioned above may be employed.

The amount of the polyhydric alcohol according to the present invention formulated in the external agent is preferably within the range of 0.1 to 98% by weight.

As the method for preparing microcapsules of gelatin film according to the present invention, known methods may be used, such as simple coacervation, complex coacervation and other methods, but generally the complex coacervation method is employed.

Next, as the liquid hydrophobic component to be enclosed within the above gelatin film microcapsules, there may be included the animal and vegetable oils, hydrocarbon oil, ester oils, silicon oils, higher fatty acids, higher alcohols, vitamins, vitamin-like acting substances, various perfumes, as mentioned above, but these are not limited in the present invention, and any lipid-soluble starting material having a liquid appearance with a melting point lower than normal temperature (25° C.) which can be generally applied to cosmetics, drugs, quasi drugs, etc., may be employed.

Also, as the solid hydrophobic component to be enclosed in the gelatin film microcapsules, there may be included the animal and vegetable oils, hydrocarbon oils, exter oils, higher fatty acids, higher alcohols, waxes, sunscreening agents, flavors, etc., as mentioned above, but these are not limited in the present invention, and any lipid-soluble starting material having a solid or semi-solid appearance which can be applied to cosmetics, drugs, quasi drugs in general, and has a melting point higher than normal temperature, may be employed. Among the above, those having melting points not higher than normal temperature are classified as liquid hydrophobic components and those having melting points not lower than normal temperature are classified as solid hydrophobic components.

The particle size of the microcapsules according to the present invention is 50 to 100 $\mu$m.

Further, the amount of the capsules according to the present invention formulated in the external agent is preferably within the range of 0.1 to 95% by weight.

The weight ratio of the hydrophobic substance forming the capsules to gelatin film is within the range of 1:0.01 to 1:10. If the weight ratio of the hydrophobic substance and gelatin is smaller than 1:0.01, the strength of the capsule coating is remarkably lowered, whereby capsule breaking may occur during preparation of the product. On the other hand, if the weight ratio is greater than 1:10, due to an increased thickness of the wall film in the capsules, the wall film may sometimes remain after breaking to give a feeling of foreign matter to the skin.

By permitting the microcapsules to be co-present with the above polyhydric alcohol, the breaking strength of the microcapsules can be controlled to 2 to 2000 g/cm$^2$ in terms of a compression loading value obtained by a creepmeter, but the breaking strength of the capsules in the present invention is preferably in the range of 10 to 300 g/cm$^2$ for formulation into the external agent. If the breaking strength of the capsules is lower than 10 g/cm$^2$, capsule breaking may occur during preparation of the product, and if higher than 300 g/cm$^2$, breaking of capsules can be effected only with difficulty when applied onto skin, whereby the feeling during use will be remarkably degraded. The instrument for measuring the breaking strength used by the present inventors is specifically a creepmeter Rheoner RE-3305 model (produced by Yamaden Co., Ltd.), and the measurement method was carried out by compressing the capsules laid in a dense mass on a glass flat plate with the Teflon 8 mm$\phi$ columnar rod mounted on the measuring instrument under a load of 1 g per 1 second, and the breaking strength was determined by calculating the amount of the load upon rupture, calculated per 1 cm$^2$.

The above gelatin capsule film according to the present invention is amorphous per se and is transparent, and further, has a sufficient non-transmissivity relative to the materials enclosed therein.

The external treatment agent of the present invention is an external treatment agent used for cosmetics, drugs, quasi drugs, etc., and has extremely excellent use characteristics in that a strong force is not required when it is to be broken by compression during usage, and that there is no feeling of foreign matter due to remaining portions of the capsule film. Therefore, it is preferably used particularly for cosmetics having characteristics which are emphasized. For example, by formulating microcapsules with particle sizes of 50 to 100 $\mu$m having hydrophobic components enclosed therein in cosmetics such as cosmetic water, emulsions, creams, shampoos, rinses, etc., a cosmetic imparting the effects not found in the prior art can be obtained.

Embodiment (6)

As the polyhydric alcohol to be formulated in the external treatment agent of the present invention, any starting material generally used for cosmetics, drugs, quasi drugs, etc., as mentioned above, may be employed.

The amount of the polyhydric alcohol according to the present invention formulated in the external agent is preferably within the range of 0.1 to 98% by weight.

As the method for preparing microcapsules of the gelatin film according to the present invention, known methods may be used, such as simple coacervation, complex coacervation and other methods, but generally the complex coacervation method is employed.

Next, as the liquid hydrophobic component to be enclosed within the above gelatin film microcapsules, there may be included the animal and vegetable oils, hydrocarbon oil, ester oils, silicone oils, higher fatty acids, higher alcohols, vitamins, vitamin-like acting substances, various perfumes, and flavors as mentioned above, but these are not limited in the present invention, and any lipid-soluble starting material having a liquid appearance with a melting point lower than normal temperature (25° C.), which can be generally applied to cosmetics, drugs, quasi drugs, etc., may be employed.

Also, as the solid hydrophobic component to be enclosed in the gelatin film microcapsules, there may be included the animal and vegetable oils, hydrocarbon oils, ester oils, higher fatty acids, higher alcohols, waxes, and flavors, etc., as mentioned above, but these are not limited in the present invention, and any lipid-soluble starting material having a solid or semi-solid appearance which can be applied to cosmetics, drugs, quasi drugs in general, and has a melting point higher than normal temperature, may be employed. Among the above, those having melting points not higher than normal temperature are classified as liquid hydrophobic components and those having melting points not lower than normal temperature are classified as solid hydrophobic components.

The particle size of the microcapsules according to the present invention is 100 to 1000 μm.

Further, the amount of the capsules according to the present invention formulated in the external agent is preferably within the range of 0.1 to 95% by weight.

The weight ratio of the hydrophobic substance forming the capsules to gelatin film is within the range of 1:0.01 to 1:10. If the weight ratio of the hydrophobic substance and gelatin is smaller than 1:0.01, the strength of the capsule coating is remarkably lowered, whereby capsule breaking may occur during preparation of the product. On the other hand, if the weight ratio is greater than 1:10, due to an increased thickness of the wall film in the capsules, the wall film may sometimes remain after breaking to give a feeling of foreign matter to the skin.

By permitting the microcapsules to be co-present with the above polyhydric alcohol, the breaking strength of the microcapsules can be controlled to 2 to 2000 g/cm$^2$ in terms of a compression loading value obtained by a creepmeter, but the breaking strength of the capsules in the present invention is preferably in the range of 10 to 300 g/cm$^2$ for formulation into the external agent. If the breaking strength of the capsules is lower than 10 g/cm$^2$, capsule destruction may occur during preparation of the product, and if higher than 300 g/cm$^2$, destruction of capsules can be effected only with difficulty when applied onto the skin, whereby the feeling during use will be remarkably degraded. The instrument for measuring the breaking strength used by the present invention is specifically a creepmeter Rheoner RE-3305 model (produced by Yamaden Co., Ltd.), and the measurement method was carried out by compressing the capsules laid in a dense mass on a glass flat plate with a Teflon 8 mmφ columnar rod mounted on the measuring instrument under a load of 1 g per 1 second, and the breaking strength was determined by calculating the amount of the load upon rupture, calculated per 1 cm$^2$.

The above gelatin capsule film according to the present invention is amorphous per se and is transparent, and further, has a sufficient non-transmissivity relative to the materials enclosed therein.

The external treatment agent of the present invention is an external agent used for cosmetics, drugs, quasi drugs, etc., and has extremely excellent use characteristics in that a strong force is not required when it is to be broken by compression during usage, and that there is no feeling of foreign matter due to remaining portions of the capsule film. Therefore, it is preferably used particularly for cosmetics having characteristics which are emphasized. For example, by formulating microcapsules with particle sizes of 100 to 1000 μm having hydrophobic components endosed therein in cosmetics such as cosmetic water, emulsions, creams, shampoos, rinses, etc., a cosmetic imparting effects not found in the prior art can be obtained.

Embodiment (7)

As the method for preparing microcapsules of gelatin film according to the present invention, known methods may be used such as simple coacervation, complex coacervation and other methods, but generally the complex coacervation method is employed.

As the method for preparing the water-in-oil type emulsion to be enclosed within the above gelatin film capsules, any of the methods generally employed may be used, for example, a simple emulsification under a high shear pressure, an amino acid gel emulsification method utilizing the salt-out action of amino acid, and a clay emulsification method utilizing the gelling ability of organophilic clay mineral.

As the oil phase component for forming the water-in-oil type emulsion, there may be included the animal and vegetable oils, hydrocarbon oils, ester oils, silicone oils, higher fatty acids, higher alcohols, waxes, etc., as mentioned above. However, these are not limited in the present invention, and any oily starting material generally applicable for external agents such as cosmetics, drugs, quasi drugs, etc. may be employed. As the lipid-soluble skin effective component to be formulated in the oil phase portion, there may be included the animal and vegetable oils, hydrocarbon oils, ester oils, silicone oils, higher fatty acids, higher alcohols, vitamins and vitamin-like acting substances, and various flavors as mentioned above. However, these are not limited in the present invention, and any lipid-soluble starting material which can be generally applied to cosmetics, drugs, quasi drugs, etc. and is laible to be peroxidized by an induction of activated radicals by the action of light or heat may be employed.

As the aqueous phase portion constituting the water-in-oil emulsion, other than pure water, there may be included one or more kinds selected from lower alcohols such as methanol, ethanol, isopropanol: polyhydric alcohols such as ethylene glycol, propylene glycol, dipropylene glycol, glycerine, 1,3-butylene glycol, sorbitol, glucose, either alone or in combination with water; inorganic acids such as sodium chloride, potassium carbonate, sodium metaphosphate, potassium dihydrogen phosphate, sodium sulfate; acids such as hydrochloric acid, phosphoric acid, acetic acid; and bases such as sodium hydroxide, potassium hydroxide, ammonia water, but these are not limited in the present invention but can be selected depending on the purpose of use.

As the water-soluble skin effective component to be formulated in the aqueous phase portion, there may be included vitamins, hormones, and amino acids, and specific examples of these further include vitamins such as thiamine hydrochloride, pyridoxin hydrochloride, nicotinic acid amide, calcium pantothenate, biotin, inositol, ascorbic acid, sodium ascorbate, rutin; hormones such as estradiol, cortizone, prednizolone; and alanine, glycine, lysine, pyrrolidone carboxylic acid, but these are not limited in the present invention, and any water-soluble starting materials which can be employed generally for external agents such as cosmetics, drugs, quasi drugs, etc., may be used.

The particle size of the capsules applied to the present invention is 0.1 to 2000 μm. Capsules with particle sizes smaller than 0.1 μm are not preferable, because they are extremely difficult to produce. On the other hand, if the particle size is larger than 2000 μm, breaking occurs by stirring during preparation of the external agent, whereby the water-soluble and lipid-soluble effective components enclosed leak into the base for the external agent to cause autooxidation or hydrolysis. Also, when breaking is to be done by compression during use of the product, "escape" of the capsules will occur, whereby breaking cannot be easily effected, or even if broken, there is a feeling of foreign matter due to remaining portions of the capsule film, and a satisfactory product from the aspect of useability cannot be obtained.

Further, the amount of the capsules enclosing the water-in-oil emulsion therein formulated in the external treatment agent is preferably within the range of 0.1 to 95% by weight.

The weight ratio of the water-in-oil emulsion forming the capsules to gelatin is within the range of 1:10 to 100:1. If the weight ratio of the hydrophobic components to gelatin is greater than 1:10, the wall film of the capsules becomes too thick, whereby the capsules can be broken only with difficulty during application onto skin. On the other hand, if the weight ratio is smaller than 100:1, the strength of the capsule film is remarkably lowered, whereby the capsules may be broken during preparation of the product, and therefore, are not suitable for practical application.

The above gelatin capsule film of the present invention is amorphous per se and is transparent, and further, has a sufficient non-transmissivity relative to the contents enclosed therein.

The external treatment agent of the present invention has extremely excellent use characteristics in that a strong force is not required when it is to be broken by compression during usage, and that there is no feeling of foreign matter due to remaining portions of the capsule film. Therefore, it is preferably used particularly for cosmetics having characteristics which are emphasized. For example, by formulating microcapsules having lipid-soluble and water-soluble effective components enclosed therein in basic cosmetics such as emulsions or creams, or in make-up cosmetics such as foundation or lipsticks, or in hair cosmetics such as hair tonics or hair creams, a cosmetic imparting effects not found in the prior art can be obtained.

Embodiment (8)

As the hydrophobic substance to be enclosed within the microcapsules according to the present invention, there may be included the animal and vegetable oils, hydrocarbon oils, ester oils, silicone oils, higher fatty acids, higher alcohols, vitamins, vitamin-like acting substances, sunscreening agents, and various flavors as mentioned above.

In the complex coacervation method according to the present invention, as the cationic and anionic hydrophilic polymer materials, any materials may be selected, but those conventionally used are preferably employed. Specifically, gelatin is most suitable as the cationic hydrophilic polymer material, and the anionic hydrophilic polymer material may include gum arabic, sodium alginate, carboxymethyl cellulose alkali metal salts, carrageenan, maleic anhydride copolymer, acrylic anhydride copolymer, etc.

The method for producing microcapsules according to the present method comprises adding an aqueous solution of a hydrophilic polymer material having opposite charges into an aqueous solution of a heated cationic hydrophilic polymer substance to effect a complex coacervation, and then successively adding one or a mixture of two or more kinds of hydrophobic substances to effect dispersion and emulsification. Further, the emulsion is cooled according to a conventional method, and the capsule films are gelled, and thereafter, hardened with a hardening agent generally used, to be denatured into a substance which cannot be dissolved in water or other solvents.

In the simple coacervation method according to the present invention, the kind of hydrophilic polymeric material may be selected depending on the purpose, but those generally used can be employed. Specifically, polyvinyl alcohol, gelatin, casein, alkali salts, sulfated cellulose, water-soluble nylon, may be included, but particularly preferably, gelatin is used. As the substance for inducing coacervation, various electrolytes and organic compounds may be employed. As the electrolyte, inorganic and organic electrolytes in general may be included. For example, inorganic electrolytes may include water-soluble metal salts and ammonium salts of sulfuric acid, hydrochloric acid, phosphoric acid, boric acid, hydroiodic acid, carbonic acid, silicic acid, nitric acid, hydrobromic acid, and organic electrolytes may include organic acids and water-soluble metal salts or ammonium salts of organic acids, amino acids and water-soluble metal salts, quaternary ammonium salts of amino acids, etc., which can be employed singly or as a mixture of two or more thereof. As the organic compound, methanol, ethanol, phenol, resorcin, ethyl acetate, ethyl urethane, acetone, dioxane, etc., may be included, and these may be employed singly or as a mixture of two or more thereof.

In the method for producing microcapsules according to the present method, after a simple coacervation is caused by an addition of the above electrolyte or organic compound into a heated aqueous solution of a hydrophilic polymer material, one or two or more kinds of mixed hydrophobic substances are successively added to effect dispersion and emulsification. The emulsion is cooled according to conventional method, and the capsule films are gelled, followed by hardening with a hardening agent generally employed, to be denatured into a substance not soluble in water or other solvents.

The weight ratio of the water-soluble polymeric material for forming wall films with a hydrophobic substance should be desirably 1:100 or less. If the weight ratio of the hydrophobic substance to the water-soluble polymer is greater than 1:100, the strength of the microcapsule wall film will be remarkably lowered, whereby destruction may occur during capsule preparation, and further, hydrophobic substances not enclosed may be sometimes formed.

The hardening agent for making the capsule film after gellation of the capsule film may include, aldehydes such as glutaraldehyde or glyceraldehyde: tannic acid or gallic acid; or alums such as potassium alum or iron alum may be employed, but these are not limited in the invention, and any of hardening agents generally employed can be used.

The microcapsules obtained according to the present production method have particle sizes which are determined depending substantially on the sizes of the capsule core substances, and are, for example, about 1 to 2000 $\mu$m in diameter.

According to the present invention, the following effects can be advantageously obtained.

(1) The capsule-containing cosmetic of the present invention has the advantages that there is no "escape" of the capsules during usage, whereby the capsules can be easily broken and the contents leaked, that the oil component can be easily spread onto the skin, and that there is no feeling of foreign matter through remaining portions of the capsule film after breakage, and it is also a cosmetic having a good usability, and an excellent luster imparting effect and skin wettability.

(2) The cosmetic of the present invention comprises microcapsules formulated therein having advantages such that they are extremely stable and do not break when mixing is carried out during preparation of the cosmetics, that they are free from "escape" during usage and can be easily broken to enable the enclosed materials to leak out, that the oil components can be easily spread onto the skin, and that there is no feeling of foreign matter through remaining portions of capsule film after breaking, whereby it has a good usability, and as an excellent luster imparting effect and skin wettability.

(3) The water-in-oil type emulsified external agent of the present invention, by microencapsulating lipid-soluble skin effective components readily peroxidized due to the limitation of the particle size, can retain an excellent efficacy without deterioration for a long term, are extremely stable and are not broken by mixing during preparation of the external agent, and have an excellent advantage in that there is no feeling of foreign matter due to remaining portions of the capsule film after breaking during usage, and thus is a water-in-oil type emulsified external agent having a good usability and an excellent luster imparting effect and skin wettability.

(4) The external agent of the present invention comprises microcapsules formulated therein, which have the advantages of being extremely stable without breaking during preparation of the external agent observed at all, and can be broken easily without "escape" during usage to leak out the enclosed components, whereby the oil components can be easily spread onto skin, and a feeling of foreign matter due to remaining portions of the capsule film after breaking is not imparted, have a good useability and an excellent luster imparting effect and skin wettability.

(5) The external agent of the present invention comprises microcapsules formulated therein, which have the advantages of being extremely stable without breaking during preparation of the external agent observed at all, and can be broken easily without "escape" during usage to leak the enclosed components, whereby the oil components can be easily spread onto skin, and have no feeling of foreign matter due to remaining portions of the capsule film after breaking, and thus have a good useability and an excellent luster imparting effect and skin wettability.

(6) The external agent of the present invention comprises microcapsules formulated therein, which have the advantages of being extremely stable without breaking during preparation of the external agent, and can be broken easily without "escape" during usage to leak the enclosed components, whereby the oil components can be easily spread onto skin, and have no feeling of foreign matter due to remaining portions of the capsule film after breaking, and have a good useability and an excellent luster imparting effect and skin wettability.

(7) The external agent of the present invention, by formulating a water-in-oil type emulsion of an oil phase containing lipid-soluble skin effective components reaidly peroxidized and an aqueous phase containing water-soluble skin effective components readily hydrolyzed enclosed within microcapsules, can retain an excellent efficacy without deterioration of the lipid-soluble and water-soluble skin effective components for a long term, and can microencapsulate both components at the same time, and therefore, is very cost-advantageous and labor-saving, and further, the water-soluble effective components enclosed will not migrate into the base of the external agent by passing through the film, and yet the contents can be easily leaked by destruction without "escape" of the microcapsules, and have advantages such that oil components and aqueous components can be easily spread onto the skin and that there is no feeling of foreign matter through remaining portions of the capsule film after destruction, have an entirely novel appearance and usability not found in the prior art, and an excellent luster imparting effect and skin wettability.

(8) According to the microcapsule production method of the present invention, in the complex coacervation method and the simple coacervation method, many kinds of hydrophobic substances with different properties can be microencapsulated in one step, whereby the operations of production, washing, etc., can be carried out at one time, which is extremely effective for reducing the time and labor required.

Also, even if a large number of different kinds of hydrophobic substances are added, microcapsules enclosing separate hydrophobic substances can be produced, and therefore, a simultaneous preparation of substances having a high reactivity is possible and applications over a wide range can be expected.

EXAMPLES

The present invention will now be further illustrated by, but is by no means limited to, the following Examples, wherein all parts and percentages are expressed on a weight basis unless otherwise noted.

EXAMPLE 1-1

To a solution of 10 g of acid-treated gelatin and 10 g of gum arabic dissolved in 200 g of purified water of 40° C. was added 150 g of squalane, and the mixture was stirred by a propeller stirring machine at 300 rpm. Further, a 10% aqueous acetic acid was dropwise added to the oil droplet dispersion, the pH was adjusted to 4.3, and the solution was diluted by an addition of 600 g of purified water at 40° C. Subsequently, cooling was effected externally of the vessel, while stirring, and 20 g of 10% aqueous potassium alum solution was added at a liquid temperature of 8° C., followed by stirring for 2 hours to harden the capsule film.

The product thus obtained was separated from the aqueous phase by decantation, and by repeating the water washing, capsules with an average particle size of 700 μm and a weight ratio of gelatin to squalane of 1:30 were obtained.

The capsules were formulated according to the recipe as shown below to obtain a transparent gel-like cosmetic water having a viscosity of 3000 cps. The viscosity was measured by a B type viscometer Model B8L manufactured by Tokyo Seiki Co., Ltd. using a rotor #4 at 12 rpm, and the following method was employed.

| | |
|---|---|
| Glycerine | 5% |
| Propylene glycol | 4 |
| Gelatin capsules | 5 |
| Ethanol | 10 |
| Sodium polyacrylate | 1 |
| Preservative | q.s. |
| Purified water | 75 |

As a Comparative Example, the amount of sodium polyacrylate formulated in the above recipe was lowered to 0.2%, the viscosity was lowered to 800 cps to give a gel-like cosmetic water (Comparative Example 1-1), and with the same recipe, a gel-like cosmetic water having capsules with a particle size of 100 μm comprising a film of methyl methacrylate prepared according to the in situ polymerization method described in Japanese Unexamined Patent Publication (KOKAI) No. 59-73510 was obtained (Comparative Example 1-2), and a gel-like cosmetic water having only the same amount of squalane of Example 1-1 dispersed in the recipe without formulation of the capsules (Comparative Example 1-3) was prepared, respectively, and comparative evaluations with the above Example were conducted.

The results are shown in Table 1-1. As shown in the Table, the evaluation of Example 1-1 was excellent in all items, compared with the other Examples.

TABLE 1-1

|  | Example 1-1 | Comparative Example 1-1 | Comparative Example 1-2 | Comparative Example 1-3 |
|---|---|---|---|---|
| Appearance (transparency) | ⊙ | ⊙ | x | x |
| Stability at 50° | ⊙ | ⊙ | ○ | x |
| Escape of capsules | ⊙ | x | Δ | — |
| Fracturability of capsules | ⊙ | ○ | x | — |
| Leak of squalane during application* | ⊙ | ○ | x | — |
| Smoothness during application (no foreign matter feeling) | ⊙ | ⊙ | x | — |
| Wetness of skin | ⊙ | ○ | Δ | Δ |

Considerably good ⊙  Good ○  Common Δ  Bad x
*judged as more readily leaked, since the value (squalane leak amount/squalane formulated amount) is nearer to 1.

EXAMPLE 1-2

Emulsion

Capsules prepared according to the same method as in Example 1-1 and enclosing oil components at a ratio of methylphenylsiloxane : vitamin E=1:0.1 (gelatin : enclosed material =1:20, average particle size: 500 μm) were formulated according to the following recipe to obtain a gel-like emulsion having a viscosity of 1500 cps.

| Stearic acid | 2% |
|---|---|
| Cetanol | 2 |
| Petrolatum | 3 |
| Lanolin alcohol | 2 |
| Liquid paraffin | 10 |
| Polyoxyethylene monooleic acid ester (10EO) | 2 |
| Preservative, antioxidant | q.s. |
| Glycerine | 3 |
| Propylene glycol | 5 |
| Triethanolamine | 1 |
| Gelatin capsules | 8 |
| Sodium polyacrylate | 0.5 |
| Purified water | 61.5 |

EXAMPLE 1-3

Cream

Two kinds of gelatin capsules enclosing γ-linoleic acid prepared according to the same method as in Example 1-1 (gelatin : enclosed material =1:30, average particle size: 600 μm) and gelatin capsules enclosing the oily components at a ratio of liquid paraffin : flavor=1:0.1 (gelatin : enclosed material =1:25, average particle size: 600 μm) were formulated according to the following recipe to obtain a cream having a viscosity of 18000 cps.

| Beeswax | 2% |
|---|---|
| Stearyl alcohol | 5 |
| Stearic acid | 8 |
| Squalane | 10 |
| Self-emulsification type propylene glycol monostearate | 3 |
| Polyoxyethylene cetyl ether (20EO) | 1 |
| Preservative, antioxidant | q.s. |
| Propylene glycol | 8 |
| Glycerine | 4 |
| Triethanolamine | 1 |
| Gelatin capsules (enclosed material: γ-linoleic acid) | 2 |
| Gelatin capsules (enclosed material: fluid paraffin: flavor = 1:0.01) | 10 |
| Polyethylene glycol | 0.6 |
| Purified water | 45.4 |

EXAMPLE 2-1

To a solution of 10 g of acid-treated gelatin and 10 g of gum arabic dissolved in 200 g of purified water at 60° C. was added 150 g of a hydrophobic component, and the mixture was stirred by a propeller stirring machine at 600 rpm. Further, a 10% aqueous acetic acid was added dropwise to the dispersion, to adjust the pH to 4.3, followed by dilution with an addition of 600 g of purified water at 40° C. Subsequently, cooling was effected externally of the vessel, while stirring, and 10 g of a 25% aqueous glutaraldehyde was added at a liquid temperature of 8° C. and the mixture was stirred for 2 hours to harden the capsule film.

The product thus obtained was separated from the aqueous phase by decantation, and water washing was repeated, and thereafter, excess water was removed by a 200 mesh sieve to obtain capsules with an average particle size of 300 μm.

The three kinds, A to C, shown below were used as the hydrophobic components enclosed within the capsules, and the capsules prepared had breaking strengths of 16, 70, and 170, respectively. Also, the capsules enclosing the hydrophobic components D to G, shown below, and having breaking strengths of 984, 685, 408, and 4, respectively, were prepared according to the same method, for comparison. For seven such capsules, a comparative evaluation was conducted of the breaking by mixing in a viscous base and the presence of a feeling of foreign matter during application onto the skin. The results are shown in Table 2-1.

Hydrophobic components enclosed

A. Liquid paraffin : cetostearyl alcohol=94:6
B. Liquid paraffin : beeswax=92:8
C. Liquid paraffin : solid paraffin=94:6
D. Liquid paraffin
E. Liquid paraffin : petrolatum=80:20
F. Liquid paraffin : petrolatum=60:40
G. Petrolatum Method of measuring hardness of enclosed material An M-301AR model cardmeter (produced by Iio Denki) was used as the measuring instrument, and the measurement was conducted by imposing a load of 200 g on a penetration needle having a diameter of 8 mm.

Method for measuring breaking strength

The capsules were laid on a glass flat plate and were compressed under a load of 1 g per 1 second by a Teflon 8 mm columnar rod mounted on a creepmeter Rheoner RE-3305 model (manufactured by Yamaden Co., Ltd.), and the breaking strength was determined by calculating the amount of load upon fracture, calculated per 1 $cm^2$.

Evaluation of breaking by mixing in a viscous base

Into 100 g of a highly viscous base (5000 cps in terms of the value measured by a Brookfield type rotatary viscometer) obtained by neutralization of a 1% aqueous sodium polyacrylate, 10 g of capsules were formulated and the occurrence of capsule breaking after stirring and mixing by a propeller stirring machine for 5 minutes was observed and evaluated by an optical microscope. The evaluation method was conducted by rating in the three ranks:
○: no breaking observed
Δ: slight breaking observed
x: substantially all capsules broken Evaluation of feeling of foreign matter by application onto the skin Each sample was applied on the skin at the innerside portion of forearm, feeling of foreign matter during rubbing with palms was represented by overall evaluation according to organoleptic test by a panel of 10 members. The evaluation was conducted at the 3 ranks shown below.
○: no feeling of foreign matter at all
Δ: slight feeling of foreign matter
x: extreme feeling of foreign matter

TABLE 2-1

|  | A | B | C | D | E | F | G |
|---|---|---|---|---|---|---|---|
| Hardness of enclosed matter (g) | 6 | 6 | 5 | 0 | 1 | 6 | 24 |
| Breaking strength of capsules (g/cm²) | 16 | 70 | 170 | 984 | 685 | 408 | 4 |
| Capsule breaking by mixing | o | o | o | o | o | o | x |
| Foreign matter feeling during application onto skin | o | o | o | x | x | Δ | o |

As shown in Table 2-1, upon evaluation, the capsules A to C having breaking strengths in the range of 10 to 300 g/cm² were found to be excellent in all of the items, compared with the other capsules D to G.

EXAMPLE 2-2 AND COMPARATIVE EXAMPLE 2-1

Capsules were prepared according to the same method as in Example 2-1 by using a mixture of squalane : solid paraffin=90:10 and only squalane for comparison as the hydrophobic component, and were classified by sieving into four kinds of capsule groups of 50 to 150 μm, 150 to 250 μm, 250 to 350 μm, and 350 to 500 μm, and the breaking strength of the respective capsules was measured.

TABLE 2-2

| Capsule particle size (μm) | Enclosed matter | |
|---|---|---|
|  | Example 2-2 Squalane + Solid paraffin | Comparative Example 2-1 Squalane |
| 50–150 | 163 | 1093 |
| 150–250 | 146 | 972 |
| 250–350 | 140 | 773 |
| 350–500 | 125 | 512 |

As shown in Table 2-2, the capsules enclosing only squalane had a breaking strength which greatly differed, depending on the particle size, and became extremely high as the particle size became smaller, but when a solid paraffin was mixed at a ratio of 10%, there was substantially no difference in breaking strength depending on the particle size, and a substantially constant value was exhibited.

EXAMPLE 2-3

Five kinds of capsules, A to F, obtained in Example 1 were formulated according to the recipe as shown below to prepare a transparent gel-like cosmetic water, and each sample was applied on the skin at the innerside portion of the forearm, and the difficulty of escape of the capsules during rubbing with the palms of the hands, fracturability of the capsules, leakage of the enclosed material during application, smoothness during application, and skin wetness were evaluated overall, according to organoleptic test by a panel of 10. The evaluation was divided into the 4 rankings shown below.
⊙: very good
○: good
Δ: average
x: poor

| Glycerine | 5% |
|---|---|
| Propylene glycol | 4 |
| Gelatine capsules | 5 |
| Ethanol | 10 |
| Sodium polyacrylate | 1 |
| Preservative | q.s. |
| Purified water | 75 |

TABLE 2-3

|  | A | B | C | D | E | F |
|---|---|---|---|---|---|---|
| Escape of capsules | ⊙ | ⊙ | ⊙ | x | x | Δ |
| Fracturabilty of capsules | ⊙ | ⊙ | ⊙ | x | x | Δ |
| Leakage of enclosed matter during application | ⊙ | ⊙ | ⊙ | x | Δ | Δ |
| Smoothness during application (no foreign matter feeling) | ⊙ | ⊙ | ⊙ | x | x | Δ |
| Wetness of skin | ⊙ | ⊙ | ⊙ | Δ | Δ | o |

*judged as more readily leaked, since the value (enclosed material leaded amount/enclosed material formulated amount) is nearer to 1.

As apparent from Table 2-3, the three samples A, B and C were found to be excellent in all of the items, compared with the others.

EXAMPLE 2-4

Emulsion

Capsules prepared according to the same method as in Example 1 enclosing the oil components of liquid paraffin : cetanol : vitamin a palmitate=92:7:1 (average particle size: 200 μm, breaking strength: 25 g/cm$^2$) were formulated according to the recipe shown below to obtain an emulsion.

| Stearic acid | 5% |
|---|---|
| Cetanol | 2 |
| Lanolin alcohol | 3 |
| Liquid paraffin | 2 |
| Polyoxyethylene monooleic acid ester (10ED) | 10 |
| Preservative, antioxidant | q.s. |
| Glycerine | 3 |
| Propylene glycol | 5 |
| Triethanolamine | 1 |
| Gelatin capsules | 8 |
| Purified water | balance |

EXAMPLE 2-5

Cream

Two kinds of gelatin capsules A prepared according to the same method as in Example 2-1 enclosing oil components of cetyl isooleate : microcrystalline was : γ-linoleic acid=90:9:1 (average particle size: 700 μm, breaking strength: 40 g/cm$^2$) and gelatin capsules B enclosing oil components of neopentylglycol didecanoate : glycerine trimyristate : flavor=60:30:10 (weight ratio) (average particle size: 150 μm, breaking strength: 186 g/cm$^2$) were formulated according to the following recipe to obtain a cream.

| Beeswax | 2% |
|---|---|
| Stearyl alcohol | 5 |
| Stearic acid | 8 |
| Squalane | 10 |
| Self-emulsification type propylene glycol monostearate | 3 |
| Polyoxyethylene cetyl ether (20EO) | 1 |
| Preservative, antioxidant | q.s. |
| Propylene glycol | 8 |
| Glycerine | 4 |
| Triethanolamine | 1 |
| Gelatin capsules A | 2 |
| Gelatin capsules B | 10 |
| Polyethylene glycol | 0.6 |
| Purified water | balance |

EXAMPLE 2-6

Shampoo

Gelatin capsules prepared according to the same method as in Example 2-1 enclosing oil components of dimethylpolysiloxane : fluid paraffin : beeswax=60:32:8 (weight ratio) (average particle size: 500 μm, breaking strength: 80 g/cm$^2$) were formulated according to the following recipe to obtain a shampoo.

| AES-Na | 16% |
|---|---|
| Lauric acid diethanolamide | 4 |
| Propylene glycol | 2 |
| Gelatin capsules | 6 |
| Preservative, dye, flavor | q.s. |
| Purified water | balance |

EXAMPLE 2-7

Rinse

Gelatin capsules prepared according to the same method as in Example 2-1 enclosing oil components of squalane : hardened oil : palm kernel oil : vitamin E=69:21:9:1 (weight ratio) (average particle size: 400 μm, breaking strength: 100 g/cm$^2$) were formulated according to the recipe shown below to obtain a rinse.

| Stearyltrimethylammonium chloride | 2% |
|---|---|
| Cetostearyl alcohol | 3 |
| Glyceryl monostearate | 1.5 |
| Sodium chloride | 0.2 |
| Gelatin capsules | 4 |
| Purified water | balance |

An evaluation was made of the gelatin capsule formulations prepared as described above. The samples used for evaluation were respectively those of Examples 2-4 to 2-7, and of Comparative Examples 2-2 to 2-5 shown below. The evaluation was conducted by applying each sample on the skin at the inner side of the forearm, and the escape of the capsules when rubbed with the palms of the hands, fracturability of the capsules, leak of the enclosed material during application, smoothness during application and, skin wetness were evaluated overall according to an organoleptic test, by a panel of 10. The evaluation was divided into the four rankings shown below:

⊚: very good
○: good
△: average
x: poor

COMPARATIVE EXAMPLE 2-2

Capsules in which the cetanol in the gelatin capsules in Example 2-4 was replaced with the same amount of fluid paraffin (breaking strength: 980 g/cm$^2$) were formulated into the emulsion recipe.

COMPARATIVE EXAMPLE 2-3

Capsules in which the microcrystalline wax in the gelatin capsules A in Example 2-5 was replaced with the same amount of cetyl isooleate (breaking strength: 492 g/cm$^2$) and the capsules in which the glycerine trimyristate in the gelatin capsules B was replaced with the same amount of neopentylglycol didecanoate (breaking strength: 1210 g/cm$^2$), were formulated into the cream recipe.

COMPARATIVE EXAMPLE 2-4

The capsules in which the beeswax in the gelatin capsules of Example 2-6 was replaced with the same amount of liquid paraffin (breaking strength: 543 g/cm$^2$) were formulated into the shampoo recipe.

COMPARATIVE EXAMPLE 2-5

The capsules in which the hardened oil and the palm kernel oil in the gelatin capsules in Example 2-7 was replaced with the same amount of squalane (breaking strength: 620 g/cm$^2$) were formulated into the rinse recipe.

TABLE 2-4

|  | Example | | | | Comparative Example | | | |
| --- | --- | --- | --- | --- | --- | --- | --- | --- |
|  | 2-4 | 2-5 | 2-6 | 2-7 | 2-2 | 2-3 | 2-4 | 2-5 |
| Escape of capsules | ⊚ | ⊚ | ⊚ | ⊚ | x | x | Δ | Δ |
| Fracturability of capsules | ⊚ | ○ | ⊚ | ⊚ | x | x | Δ | x |
| Leakage of enclosed matter during application* | ⊚ | ⊚ | ⊚ | ⊚ | x | x | Δ | x |
| Smoothness during application (no foreign matter feeling) | ⊚ | ○ | ⊚ | ⊚ | x | x | x | x |
| Wetness of skin | ⊚ | ⊚ | — | — | Δ | Δ | — | — |

*judged as more readily leaked, since the value (enclosed material leaked amount-/enclosed material formulated amount) is nearer to 1.

As apparent from Table 2-4, the cosmetics containing capsules having a breaking strength of 10 to 300 g/cm$^2$, obtained by mixing a solid or semi-solid oil component into the gelatin capsules formulated therein, were found to be excellent in all of the items, compared with the others.

EXAMPLE 3-1

To a solution of 5 g of acid-treated gelatin and 10 g of gum arabic dissolved in 200 g of purified water of 50° C. was added 100 g of mixed oil components of liquid paraffin : cetyl isooleate : vitamin A palmitate=60:35:5, and the mixture was stirred by a homomixer emulsifying machine at 7000 rpm. Further, to this oil droplet dispersion was added a 10% aqueous acetic acid to adjust the pH to 4.3, followed by dilution with an addition of 600 g of purified water at 50° C. Subsequently, cooling was effected externally of the vessel, while stirring, and 5 g of an aqueous 25% Glutaraldehyde was added at a liquid temperature of 8° C., followed by stirring for 2 hours to harden the capsule film.

The product thus obtained was separated from the aqueous phase by decantation, and by repeating the water washing, capsules with particle sizes of 10 to 50 μm were obtained.

The capsules were formulated according to the recipe shown below to prepare a water-in-oil type emollient lotion.

| Microcrystalline wax | 1.0 (part) |
| --- | --- |
| Beeswax | 2.0 |
| Lanolin | 2.0 |
| Liquid paraffin | 20.0 |
| Squalane | 10.0 |
| Sorbitan sesquioleic acid ester | 4.0 |
| Polyoxyethylene (20 mole) sorbitan monooleic acid ester | 1.0 |
| Flavor | 0.4 |
| Preservative | q.s. |
| Vitamin A palmitate enclosing microcapsules | 10.0 |
| Propylene glycol | 8.0 |
| Purified water | balance |

Preparation method: vitamin A palmitate enclosing microcapsules and propylene glycol were added to purified water, and the aqueous phase portion maintained at 70° C. by heating was added to the oil phase portion maintained at 70° C. by mixing and heating and dissolving other components, to effect a preliminary emulsification, followed by homogeneous emulsification by a homomixer. After the emulsification, the emulsion was stirred while being cooled.

Also, as a Comparative Example, an emollient lotion having the same amount of mixed oil components as the enclosed amount formulated in the oil phase without a formulation of microcapsules according to the above recipe (Comparative Example 3-1) was prepared, and a comparative evaluation was conducted with the above Example 3-1 with respect to the stability with a lapse of time of the vitamin A palmitate.

The experiments were conducted by storing the vessels containing the respective emollient lotions in a thermostat at 50° C., and the amount of vitamin A palmitate remaining after 7, 14, 30, and 60 days was determined.

The results are shown in FIG. 1, from which it can be seen that the reduction of vitamin A palmitate was slower in Example 3-1, compared with that in Comparative Example 3-1.

EXAMPLE 3-2

The microcapsules (particle size: 20-80 μm) prepared according to the same method as in Example 3-1, except for changing the acid-treated gelatin to 10 g, using the oil components of squalane : cetanol : flavor (linalool)=85:10:5 as the hydrophobic components to be enclosed within microcapsules, and changing the stirring speed of the homomixer to 5000 rpm, were formulated according to the following recipe to obtain an water-in-oil type cream.

| Microcrystalline wax | 9.0 (part) |
| --- | --- |
| Paraffin | 2.0 |
| Beeswax | 3.0 |
| Petrolatum | 5.0 |
| Reduced lanolin | 8.0 |
| Squalane | 34.0 |
| Hexadecylazipic acid ester | 10.0 |
| Hydrophilic glycerine monooleate | 3.5 |
| Polyoxyethylene (20 mole) sorbitan monooleic acid ester | 1.0 |
| Preservative | q.s. |
| Flavor enclosing microcapsules | 20.0 |
| Propylene glycol | 2.0 |
| Purified water | balance |

Preparation method: To purified water were added flavor-enclosing microcapsules and propylene glycol, and an aqueous phase portion heated to 70° C. was added to the oil phase portion maintained at 70° C. by mixing and dissolving, by heating other components to effect a preliminary emulsification, followed by homogeneous emulsification by a homomixer, and the emulsion was adjusted to 30° C. by a heat-exchanger.

Also, as in the Comparative Example, a water-in-oil type cream having the same amount of mixed oil components as the enclosed amount without formulation of the microcapsules according to the above recipe in the oil phase (Comparative Example 3-2) was prepared, and a comparative evaluation of the above Example was conducted with respect to the stability of the flavor with a lapse of time.

The experiments were conducted by storing the vessels containing the respective water-in-oil type creams in a thermostat of 0° C., 25° C. and 50° C., and the change in flavor after 60 days when stored at 0° C., with the Comparative Example as the standard, was represented by an overall evaluation, by the organoleptic test, by a panel of 10. The evaluation method was divided into the following 3 rankings:

○: no change in flavor
Δ: slight change in flavor
x: extreme change in flavor

TABLE 3-1

|  | 0° C. | 25° C. | 50° C. |
|---|---|---|---|
| Example 3-2 | ○ | ○ | Δ |
| Comparative Example 3-2 | ○ | Δ | x |

As shown in Table 3-1, Example 3-2 having a flavor microencapsulated was found to exhibit substantially no change in flavor at the respective temperatures, compared with the Comparative Example.

In the following, other Examples are shown which have the same excellent effects as obtained in Examples 3-1 and 3-2.

EXAMPLE 3-3

Skin lotion

Microcapsules with particle size of 30 to 80 μm prepared according to the same method as in Example 3-1 enclosing the oil components of avocado oil : estrone=95.5:0.5 were formulated according to the following recipe to obtain a skin lotion.

| Oil Phase | |
|---|---|
| Macademian nut oil | 10.0 (part) |
| Jojoba oil | 15.5 |
| Lanolin | 2.0 |
| Polyoxyethylene (10 mole) polyoxypropylene (15 mole) 2-dodecylhexadecyl ether | 3.0 |
| Butyl paraoxybenzoate | 0.1 |
| Flavor | 0.1 |
| Aqueous Phase | |
| Oil components enclosing microcapsules | 15.0 |
| Glycerine | 5.0 |
| Purified water | balance |

Preparation method: The oil phase portion was dissolved homogeneously at 70° C., and separately, the aqueous phase portion was mixed homogeneously at 70° C. The aqueous phase portion was added to the oil phase portion, while stirring, and after further emulsification by a homomixer, the emulsion was cooled, while stirring, to room temperature and filled in a vessel.

EXAMPLE 3-4

Massage cream

Microcapsules (particle size: 60 to 100 μm) prepared according to the same method as in Example 3-1 enclosing the oil components of squalane : γ-linolenic acid : vitamin E acetate=60:30:10 were formulated according to the following recipe to obtain a massage cream.

| Oil Phase | |
|---|---|
| Solid paraffin | 4.0 (part) |
| Microcrystalline wax | 6.0 |
| Beeswax | 6.0 |
| Petrolatum | 14.0 |
| Liquid paraffin | 32.5 |
| Sorbitan sesquioleic acid ester | 3.7 |
| Polyoxyethylene (20 mole) sorbitan monooleic acid ester | 0.8 |
| Flavor | 0.5 |
| Preservative | q.s. |
| Aqueous Phase | |
| Oil components enclosing microcapsules | 15.0 |
| Soap powder | 0.3 |
| Purified water | balance |

Preparation method: To the oil phase portion dissolved by heating at 70° C., the aqueous phase portion of 70° C. was added to effect preliminary emulsification, followed by homogeneous emulsification by a homomixer, and the emulsion was cooled to around room temperature by a heat-exchanger.

EXAMPLE 3-5

Cosmetic base cream

Microcapsules (particle size: 30 to 70) prepared according to the same method as in Example 3-1 containing the oil components of orange oil : riboflavin butyric acid ester=90:10 were formulated according to the following recipe to obtain a cosmetic base cream.

| Oil Phase | |
|---|---|
| Squalane | 23.0 (part) |
| Cyclic silicone | 5.0 |
| Organophilic clay mineral obtained by treating 0.5 g of bentone-38 with 0.1 g of myristoyl lecithin | 0.6 |
| Microcrystalline wax | 2.0 |
| Butyl parahydroxybenzoate | 0.1 |
| Flavor | 0.1 |
| Titanium oxide | 1.0 |
| Coloration pigment | 0.1 |
| Aqueous Phase | |
| Oil components enclosing microcapsules | 5.0 |
| Dipropylene glycol | 5.0 |
| Purified water | balance |

Preparation method: The aqueous phase portion dissolved at 70° C. was gradually added, while stirring, by a disper into the oil phase, and mixed and dispersed at 70° C. to be emulsified therein, followed by cooling.

EXAMPLE 3-6

Night cream

Microcapsules (particle size: 25 to 80 μm) prepared according to the same method as in Example 3-1 enclosing the oil components of isocetyl oleate : arachidonic acid : pyridoxyl dipalmitate=80:15:5 were formulated according to the following recipe to obtain a night cream.

| Oil Phase | |
|---|---|
| Squalane | 25.0 (part) |
| Ceresine | 3.0 |
| Microcrystalline wax | 1.5 |
| Lanolin | 0.5 |
| Petrolatum | 6.0 |
| Flavor | q.s. |
| Preservative | q.s. |
| Amino Acid W/O Gel | |
| Glycerine monooleate | 4.0 |
| Monosodium L-glutamate | 3.2 |
| Purified Water | 12.8 |
| Aqueous Phase | |
| Oil components enclosing microcapsules | 7.0 |
| Propylene glycol | 5.0 |
| Purified water | balance |

Preparation method: To purified water heated to 70° C. was added monosodium L-glutamate to be dissolved therein, and the solution was added to glycerine monooleate at 70° C. to prepare an amino acid W/O gel by a homomixer. Then, the oil phase portion and the aqueous phase portion dissolved by heating at 70° C. were added and homogeneously emulsified by a homomixer, followed by cooling by a heat-exchanger.

EXAMPLE 3-7

Foundation

Microcapsules (particle size: 5 to 50 μm) prepared according to the same method as in Example 3-1 enclosing the oil components of jojoba oil : ergocalciferol (vitamin D) : ascorbyl dipalmitate=80:15:5 were formulated according to the following recipe to obtain a foundation.

| | |
|---|---|
| Talc | 20.0 (part) |
| Titanium dioxide | 8.0 |
| Kaolin | 7.0 |
| Solid paraffin | 5.0 |
| Lanolin | 10.0 |
| Liquid paraffin | 27.0 |
| Sorbitan sesquioleic acid ester | 5.0 |
| Pigment | q.s. |
| Flavor | q.s. |
| Preservative | q.s. |
| Oil components enclosing microcapsules | 5.0 |
| Purified water | balance |

Preparation method: Talc, titanium dioxide, kaolin and pigment were mixed and treated by a pulverizer. To the powder portion were added a part of the fluid paraffin and sorbitan sesquioleic acid ester and the mixture was dispersed homogeneously by a homomixer. Other components except for purified water were then melted by heating and added thereto, and the mixture was maintained at 70° C. to form the oil phase portion. Purified water was heated to 70° C. and added to the oil phase portion, emulsified homogeneously by a homomixer, and after emulsification, cooled under mixing to 40° C.

EXAMPLE 3-8

Lipstick

Microcapsules (particle size: 2 to 20 μm) prepared according to the same method as in Example 3-1 enclosing the oil components of safflower oil : decyl oleate=75:25 were formulated according to the following recipe to obtain an emulsified lipstick.

| | |
|---|---|
| Oil Phase | |
| Castor oil | 47.0 (part) |
| Diglyceride isostearate | 10.0 |
| Candelilla wax | 8.0 |
| Solid paraffin | 10.0 |
| Polyoxyethylene (20 mole) polyoxy-propylene (20 mole) 2-tetradecyl-octadecyl ether | 4.0 |
| Pigment | |
| Red No. 202 | 1.0 |
| Red No. 204 | 0.5 |
| Titanium oxide | 1.0 |
| Red iron oxide | 1.5 |
| Yellow iron oxide | 1.0 |
| Aqueous Phase | |
| Oil components enclosing microcapsules | 5.0 |
| Glycerine | 3.0 |
| Purified water | balance |

Preparation method: The oil phase portion was homogeneously dissolved at 80° C., and the pigments were added thereto to be dispersed therein, and further, the aqueous phase was added to effect emulsification. Then, while stirring, the emulsion was filled into a molding vessel and cooled.

EXAMPLE 3-9

Emulsified cheek rouge

Microcapsules (particle size: 8 to 50 μm) prepared according to the same method as in Example 3-1 enclosing the oil components of macademia nut oil : pantothenyl ethyl ether=95:5 were formulated according to the following recipe to obtain an emulsified face rouge.

| | |
|---|---|
| Oil Phase | |
| 2-ethylhexanoic acid triglyceride | 20.0 (part) |
| Hydrogenated lanolin | 15.0 |
| Microcrystalline wax | 5.0 |
| Polyoxyethylene (15 mole) polyoxy-propylene (30 mole) 2-octyldodecyl ether | 3.0 |
| Pigment | |
| Talc | 20.0 |
| Titanium oxide | 5.0 |
| Red iron oxide | 3.0 |
| Yellow iron oxide | 1.0 |
| Black iron oxide | 0.1 |
| Red No. 201 | 1.0 |
| Butyl paraoxybenzoate | 0.1 |
| Flavor | 0.1 |
| Aqueous Phase | |
| Oil components enclosing microcapsules | 5.0 |
| Glycerine | 5.0 |

Preparation method: The oil phase was dissolved homogeneously at 80° C., the pigments were added to be dispersed therein, and further, the aqueous phase was added to effect emulsification. While stirring, the emulsion was case into a vessel and cooled.

EXAMPLE 3-10

Hair cream oil

Microcapsules (particle size: 15 to 45 μm) prepared according to the same method as in Example 3-1 enclosing the oil components of avocado oil : linoleic acid : phytosterol=85:10:5 were formulated according to the following recipe to obtain a hair cream oil.

| | |
|---|---|
| Oil Phase | |
| Liquid paraffin | 30.0 (part) |
| Microcrystalline wax | 3.0 |
| Polyoxyethylene (8 mole) polyoxy-propylene (8 mole) 2-octyldodecyl ether | 5.0 |
| Butyl benzoate | 0.1 |
| Flavor | 0.1 |
| Aqueous Phase | |
| Oil components enclosing microcapsules | 15.0 |
| Purified water | balance |

Preparation method: The oil phase portion was homogeneously mixed at 70° C., and separately, the aqueous phase portion was heated to 70° C. The aqueous phase portion was added, while stirring, into the oil phase portion, and further, the mixture was emulsified by a homomixer and then cooled to room temperature and filled in a vessel.

Next, an evaluation was made of the cosmetics having microcapsules formulated therein and prepared as described above. The samples used for the evaluation were, respectively, samples of Example 3-3 to 3-10 and the following Comparative Examples 3-3 to 3-10. The evaluation method was conducted by observing the destruction of microcapsules during the cosmetic preparation by an optical microscope, and evaluated according to the following four rankings:

⊚: no breakage
○: slight breakage
Δ: substantial breakage and broken film observed
x: complete breakage and no trace of film.

Also, each sample was applied on the skin at the inside portion of the forearm, and the feeling of foreign matter through remaining portions of the capsule film when rubbed by the palms of the hands was subjected to an overall evaluation, by an organoleptic test by a panel of 10, according to the following three rankings:

○: no feeling of foreign matter
Δ: slight feeling of foreign matter
x: extreme feeling of foreign matter.

COMPARATIVE EXAMPLE 3-3

The microcapsules of Example 3-3 were prepared by propeller stirring at 600 rpm (particle size: 200 to 400 μm) and formulated according to the skin lotion recipe.

COMPARATIVE EXAMPLE 3-4

The microcapsules of Example 3-4 were prepared by propeller stirring at 400 rpm (particle size: 400 to 700 μm) and formulated according to the massage cream recipe.

COMPARATIVE EXAMPLE 3-5

The microcapsules of Example 3-5 were prepared by propeller stirring at 300 rpm (particle size: 500 to 1000 μm) and formulated according to the cosmetic base cream recipe.

COMPARATIVE EXAMPLE 3-6

The microcapsules of Example 3-6 were prepared by propeller stirring at 350 rpm (particle size: 400 to 800 μm) and formulated according to the night cream recipe.

COMPARATIVE EXAMPLE 3-7

The microcapsules of Example 3-7 were prepared by propeller stirring at 800 rpm (particle size: 120 to 250 μm) and formulated according to the foundation recipe.

COMPARATIVE EXAMPLE 3-8

The microcapsules of Example 3-8 were prepared by propeller stirring at 750 rpm (particle size: 150 to 350 μm) and formulated according to the lipstick recipe.

COMPARATIVE EXAMPLE 3-9

The microcapsules of Example 3-9 were prepared by propeller stirring at 550 rpm (particle size: 200 to 400 μm) and formulated according to the emulsified check rouge recipe.

COMPARATIVE EXAMPLE 3-10

The microcapsules of Example 3-10 were prepared by propeller stirring at 250 rpm (particle size: 450 to 1000 μm) and formulated according to the hair cream oil recipe.

TABLE 3-2

|  |  | Breakage during preparation | Breakage during usage |
|---|---|---|---|
| Example | 3-3 | ⊚ | ○ |
|  | 3-4 | ⊚ | ○ |
|  | 3-5 | ⊚ | ○ |
|  | 3-6 | ⊚ | ○ |
|  | 3-7 | ⊚ | ○ |
|  | 3-8 | ⊚ | ○ |
|  | 3-9 | ⊚ | ○ |
|  | 3-10 | ○ | ○ |
| Comparative | 3-3 | ○ | Δ |
| Example | 3-4 | Δ | x |
|  | 3-5 | Δ | x |
|  | 3-6 | Δ | x |
|  | 3-7 | Δ | Δ |
|  | 3-8 | x | Δ |
|  | 3-9 | x | x |
|  | 3-10 | Δ | x |

As apparent from Table 3-2, the cosmetics having microcapsules with particle sizes of 100 μm or less were found to be excellent in all of the items, compared with the cosmetics having capsules larger than 100 μm.

EXAMPLE 4-1

To a solution of 10 g of acid-treated gelatin and 10 g of gum arabic dissolved in 200 g of purified water of 60° C. was added 150 g of squalane, and the mixture was stirred by a propeller stirring machine at 1300 rpm. Further, 10% aqueous acetic acid was added dropwise to the dispersion to adjust the pH to 4.3, followed by dilution with an addition of 600 g of purified water of 40° C. Subsequently, cooling was effected externally of the vessel, while stirring, and 10 g of 25% aqueous glutaraldehyde was added at a liquid temperature of 8° C. and the mixture was stirred for 2 hours to harden the capsule film.

The product thus obtained was separated from the aqueous phase by decantation, and water washing was repeated, and thereafter, excess water was removed by screening to obtain capsules with an average particle size of 40 μm.

The microcapsules were dispersed to 10% in terms of weight ratio in solutions with seven kinds of compositions of glycerine : water=0:100, 10:90, 20:80, 30:70, 40:60, 60:40, 80:20, and then formulated according to the recipes shown below to prepare emollient lotions, and the breakage by stirring during preparation and feeling of foreign matter when applied onto the skin were then evaluated, by comparison.

Also, microcapsules were removed from the emollient lotion and the breaking strength thereof measured.

| Oil Phase | |
|---|---|
| Squalane | 5.0 parts |
| Petrolatum | 2.0 |
| Beeswax | 0.5 |
| Sorbitane sesquioleic acid ester | 0.8 |
| Polyoxyethylene (20 mol) oleyl ether | 1.2 |
| Flavor | 0.5 |
| Preservative | q.s. |

-continued

| Aqueous Phase | |
|---|---|
| Microcapsule dispersion | 20.0 |
| Ethanol | 5.0 |
| Carboxyvinyl polymer (1.0% aqueous solution) | 20.0 |
| Potassium hydroxide | 0.1 |
| Purified water | balance |

Preparation method: To purified water were added the microcapsule dispersion and ethanol, the mixture was heated to 70° C., and to this mixture was added the oil phase portion dissolved at 70° C. to effect preliminary emulsification, followed by homogeneous emulsification by a homomixer with an addition of the carboxyvinyl polymer and potassium hydroxide, and thereafter, the emulsion was cooled to 30° C. by a heat-exchanger.

The respective experiments were conducted according to the following methods.

Evaluation of breakage during lotion preparation

Breakage of capsules in the emollient lotion prepared according to the above recipe and method was observed by an optical microscope.

The evaluation method was conducted according to the three ranks:
○: no breakage observed
Δ: slight breakage observed
x: breakage of all capsules Evaluation of feeling of foreign matter upon application to the skin The emollient lotions formulated with the respective capsules were applied onto the skin on the inner side portion of the forearm, and feeling of foreign matter when rubbed with the palms of the hands was represented in terms of overall evaluation, by an organoleptic test by a panel of 10. The evaluation was divided into the three rankings:
○: no foreign matter feeling
Δ: slight foreign matter feeling
x: extreme foreign matter feeling Take-out of capsules The emollient lotion was centrifugated at 5000 rpm and the microcapsules floating in the upper portion were taken out.

Method for measuring breaking strength

The same method as mentioned above.

TABLE 4-1

| | | | | | | | |
|---|---|---|---|---|---|---|---|
| Glycerine | 0 | 10 | 20 | 30 | 40 | 60 | 80 |
| Water | 100 | 90 | 80 | 70 | 60 | 40 | 20 |
| Capsule breakage during preparation | ○ | ○ | ○ | ○ | ○ | ○ | ○ |
| Foreign matter feeling during application on skin | x | x | Δ | ○ | ○ | ○ | ○ |
| Breaking strength of capsules (g/cm²) | 1056 | 867 | 472 | 205 | 121 | 73 | 49 |

As shown in Table 4-1, the microcapsules having a breaking strength in the range of 10 to 300 g/cm² were found to be excellent in all of the items, compared with other microcapsules.

EXAMPLE 4-2

Microcapsules enclosing a liquid paraffin with an average particle size of 32 μm were prepared according to the same method as in Example 4-1, except that the stirrer was replaced by a homomixer and the stirring speed was made 1200 rpm.

The microcapsules were dispersed to 15% in terms of weight ratio in solutions with 7 kinds of compositions of propylene glycol : water=0:100, 10:90, 20:80, 30:70, 40:60, 60:40, 80:20, and then formulated according to the recipes shown below to prepare transparent gel-like cosmetic waters, and the difficulty of escape of capsules, ease of rupture of capsules, ease of leakage of enclosed matter during application, smoothness during application and skin wetness when the respective samples were applied onto the skin on the innerside of the forearm were represented by an overall evaluation, by an organoleptic test, by a panel of 10.

The evaluation was divided into the following 4 rankings:
⊚: very good
○: good
Δ: average
x: poor The breaking strength of microcapsules taken out of the gel-like cosmetic water was measured at the same time.

| | |
|---|---|
| Microcapsule dispersion | 20.0 parts |
| Oleyl alcohol | 4.0 |
| Polyoxyethylene (20 mol) sorbitane monolauric acid ester | 1.5 |
| Polyoxyethylene (20 mol) lauryl ether | 0.5 |
| Ethanol | 10.0 |
| Sodium polyacrylate | 1.0 |
| Flavor | 0.1 |
| Preservative | q.s. |
| Purified water | balance |

TABLE 4-2

| | | | | | | | |
|---|---|---|---|---|---|---|---|
| Propylene glycol | 0 | 10 | 20 | 30 | 40 | 60 | 80 |
| Water | 100 | 90 | 80 | 70 | 60 | 40 | 20 |
| Difficulty of escape of capsules | x | x | Δ | ○ | ⊚ | ⊚ | ⊚ |
| Ease of rupture of capsules | x | x | ○ | ○ | ⊚ | ⊚ | ⊚ |
| Ease of leakage of enclosed matter during application* | x | x | Δ | ○ | ⊚ | ⊚ | ⊚ |
| Smoothness during application (no foreign matter feeling) | x | x | x | ○ | ⊚ | ⊚ | ⊚ |
| Skin wetness | x | x | Δ | ○ | ⊚ | ⊚ | ⊚ |
| Breaking strength of capsules (g/cm²) | 1145 | 899 | 504 | 261 | 158 | 97 | 55 |

*judged as more readily leaked out, since the value (leaked amount of enclosed matter/enclosed matter formulated) is nearer to 1.

As shown in Table 4-2, the capsules having a breaking strength within the range of 10 to 300 g/cm² were found to be excellent in all the items, compared with other capsules.

EXAMPLE 4-3

Cream

Microcapsules (average particle size 6 μm) enclosing oil components at a ratio of fluid paraffin : vitamin A palmitate=92:8 prepared by the same method as in Example 1, but changing the stirring speed by a homomixer to 4000 rpm, were dispersed to a weight ratio of 40% in a solution with a composition of propylene glycol : glycerine : water=50:20:30, and formulated according to the following recipe to obtain a cream.

The breaking strength of the microcapsules taken out of the cream was found to be 242 g/cm².

| Beeswax | 2.0 parts |
|---|---|
| Stearyl alcohol | 5.0 |
| Stearic acid | 8.0 |
| Squalane | 10.0 |
| Self-emulsification type propylene glycol monostearate | 3.0 |
| Polyoxyethylene cetyl ether (20 EO) | 1.0 |
| Preservative, antioxidant | q.s. |
| Triethanolamine | 1.0 |
| Microcapsule dispersion | 20.0 |
| Polyethylene glycol | 0.6 |
| Purified water | balance |

EXAMPLE 4-4

Shampoo

Microcapsules (average particle size 22 μm) enclosing oil components at a ratio of dimethylpolysiloxane : liquid paraffin=60:40 (weight ratio) prepared according to the same method as in Example 4-1, but changing the stirring speed by a homomixer to 1800 rpm, were dispersed to 15% in a solution with a composition of 1,3-butylene glycol : water=40:60, and formulated according to the following recipe to obtain a shampoo.

The breaking strength of the microcapsules taken out of the shampoo was found to be 236 g/cm².

| AES-Na | 16.0 parts |
|---|---|
| Lauric acid diethanolamide | 4.0 |
| Microcapsule dispersion | 18.0 |
| Preservative, dye, flavor | q.s. |
| Purified water | balance |

EXAMPLE 4-5

Rinse

Microcapsules (average particle size 15 μm) enclosing oil components at a ratio of squalane : vitamin E=95:5 (weight ratio) prepared according to the same method as in Example 1, but changing the stirring speed by a homomixer to 2500 rpm, were dispersed to 40% in a solution with a composition of propylene glycol : polyethylene glycol : water=45:5:50, and formulated according to the following recipe to obtain a rinse.

The breaking strength of the microcapsules taken out of the rinse was found to be 158 g/cm².

| Stearyl trimethyl ammonium chloride | 2.0 parts |
|---|---|
| Cetostearyl alcohol | 3.0 |
| Glyceryl monostearate | 1.5 |
| Sodium chloride | 0.2 |
| Microcapsule dispersion | 25.0 |
| Purified water | balance |

EXAMPLE 4-6

Microcapsules (average particle size 10 μm) enclosing oil components at a ratio of fluid paraffin : vitamin C stearate=96:4 (weight ratio) prepared according to the same method as in Example 4-1, but changing the stirring speed by a homomixer to 3000 rpm, were dispersed to 15% in a solution with a composition of glycerine : sucrose : water=70:5:25, and formulated according to the following recipe to obtain a foundation.

The breaking strength of the microcapsules taken out of the foundation was found to be 145 g/cm².

| Stearic acid | 5.0 parts |
|---|---|
| Lipophilic glycerine monostearate | 2.5 |
| Cetostearyl alcohol | 1.0 |
| Propylene glycol monolaurate | 3.0 |
| Fluid paraffin | 4.0 |
| Isopropyl myristate | 9.0 |
| Butyl p-oxybenzoate | q.s. |
| Flavor | q.s. |
| Titanium oxide | 8.0 |
| Kaolin | 5.0 |
| Talc | 2.0 |
| Bentonite | 1.0 |
| Colored pigment | q.s. |
| Microcapsule dispersion | 12.0 |
| Triethanolamine | 1.2 |
| Sorbitol | 3.0 |
| Methyl p-oxybenzoate | q.s. |
| Purified water | balance |

The cosmetics formulated with the microcapsules as prepared above were evaluated.

The samples used for evaluation were the respective samples of Examples 4-3 to 4-6 and the following Comparative Examples 4-1 to 4-4.

The evaluation method was based on the difficulty of escape of the capsules, ease of rupture of the capsules, ease of leakage of enclosed matter during application, smoothness during application and skin wetness when the respective samples were applied to the skin on the innerside of the forearm, by an overall evaluation, by an organoleptic test, by a panel of 10.

The evaluation was divided into the following 4 rankings:

⊚: very good
○: good
△: average
x: poor

COMPARATIVE EXAMPLE 4-1

A formulation of a cream recipe was obtained by replacing propylene glycol and glycerine with an equal amount of water in the solution for dispersion of the microcapsules in Example 4-3. (The breaking strength of the microcapsules taken out of the cream was 2127 g/cm².)

COMPARATIVE EXAMPLE 4-2

A formulation of a shampoo recipe was obtained by changing the composition for dispersing the microcapsules in Example 4-4 to 1,3-butylene glycol : water=25:75. (The breaking strength of the microcapsules taken out of the shampoo was 543 g/cm².)

COMPARATIVE EXAMPLE 4-3

A formulation of the rinse recipe was obtained by changing the composition of the solution for dispersing the microcapsules in Example 4-5 to propylene glycol : polyethylene glycol : water=20:5:75. (The breaking strength of the microcapsules taken out of the rinse was 608 g/cm².)

COMPARATIVE EXAMPLE 4-4

A formulation of a foundation recipe was obtained by replacing glycerine and sucrose in the solution for dispersing the microcapsules in Example 4-6 with an equal amount of water. (The breaking strength of the microcapsules taken out of the foundation was 1316 g/cm².)

TABLE 4-3

|  | Example | | | | Comparative Example | | | |
|---|---|---|---|---|---|---|---|---|
|  | 4-3 | 4-4 | 4-5 | 4-6 | 4-1 | 4-2 | 4-3 | 4-4 |
| Difficulty of escape of capsules | ⊚ | ⊚ | ⊚ | ⊚ | x | Δ | x | x |
| Ease of rupture of capsules | ○ | ⊚ | ⊚ | ○ | x | x | x | x |
| Ease of leakage of enclosed matter during application* | ○ | ⊚ | ⊚ | ○ | x | x | x | x |
| Smoothness during application (no foreign matter feeling) | ⊚ | ⊚ | ⊚ | ⊚ | x | x | x | x |

*judged as more readily leaked out, since the value (leaked amount of enclosed matter/enclosed matter formulated) is nearer to 1.

As apparent from Table 4-3, the cosmetics formulated with the capsules controlled to a breaking strength of 10 to 300 g/cm² by mixing microcapsules and polyhydric alcohol were found to be more excellent in all of the items, compared with others.

EXAMPLE 5-1

To a solution of 10 g of acid-treated gelatin and 10 g of gum arabic dissolved in 200 g of purified water of 60° C. was added 150 g of squalane, and the mixture was stirred by a propeller stirring machine at 1000 rpm. Further, 10% aqueous acetic acid was added dropwise to the dispersion to adjust the pH to 4.3, followed by dilution with an addition of 600 g of purified water at 40° C. Subsequently, cooling was effected externally of the vessel while stirring, and 10 g of 25% aqueous glutaraldehyde was added at a liquid temperature of 8° C. and the mixture was stirred for 2 hours to harden the capsule film.

The product thus obtained was separated from the aqueous phase by decantation, and water washing was repeated, and thereafter, excess water was removed by screening to obtain capsules with an average particle size of 70 μm.

The microcapsules were dispersed to 10% in terms of weight ratio in solutions with seven kinds of compositions of glycerine : water=0:100, 10:90, 20:80, 30:70, 40:60, 60:40, 80:20, and then formulated according to the recipes shown below to prepare transparent gel-like cosmetic waters, and breakage by stirring during preparation and a feeling of foreign matter when applied onto the skin were evaluated, by comparison.

Also, microcapsules were taken out of the transparent gel-like cosmetic water and the breaking strength thereof measured.

| Microcapsule dispersion | 20.0 parts |
|---|---|
| Oleyl alcohol | 4.0 |
| Polyoxyethylene (20 mol) sorbitane monolauric acid ester | 1.5 |
| Polyoxyethylene (20 mol) lauryl ether | 0.5 |
| Ethanol | 10.0 |
| Sodium polyacrylate | 1.0 |
| Flavor | 0.1 |
| Preservative | q.s. |
| Purified water | balance |

The respective experiments were conducted according to the following methods.

Evaluation of breakage during cosmetic water preparation

The breakage of capsules in the transparent gel-like cosmetic water prepared according to the above recipe was observed by an optical microscope.

The evaluation was divided into the following three rankings:
○: no breakage observed
Δ: slight breakage observed
x: all capsules broken Evaluation of feeling of foreign matter upon application to the skin The cosmetic waters formulated with the respective capsules were applied onto the skin on the inner side portion of the forearm, and a feeling of foreign matter was represented in terms of an overall evaluation, by an organoleptic test by a panel of 10. The evaluation was divided into the following three rankings:
○: no foreign matter feeling
Δ: slight foreign matter feeling
x: extreme foreign matter feeling Take-out of capsules The transparent gel-like cosmetic water was centrifugated at 4000 rpm and the microcapsules floating at the upper portion were taken out.

Method for measuring breaking strength

The same method as mentioned above.

TABLE 5-1

| Glycerine | 0 | 10 | 20 | 30 | 40 | 60 | 80 |
|---|---|---|---|---|---|---|---|
| Water | 100 | 90 | 80 | 70 | 60 | 40 | 20 |
| Capsule breakage during preparation | ○ | ○ | ○ | ○ | ○ | ○ | ○ |
| Foreign matter feeling during application on skin | x | x | Δ | ○ | ○ | ○ | ○ |
| Breaking strength of capsules (g/cm²) | 1080 | 606 | 368 | 185 | 103 | 59 | 28 |

As shown in Table 5-1, the microcapsules having a breaking strength in the range of 10 to 300 g/cm² were found to be excellent in all of the items, compared with other microcapsules.

EXAMPLE 5-2

Microcapsules enclosing a liquid paraffin with an average particle size of 85 μm were prepared according to the same method as in Example 5-1, except the stirrer was replaced by a homomixer and the stirring speed changed to 850 rpm.

The microcapsules were dispersed to 15% in terms of weight ratio in solutions with 7 kinds of compositions of propylene glycol : water=0:100, 10:90, 20:80, 30:70, 40:60, 60:40, 80:20, and then formulated according to the recipe shown below to prepare emollient lotions, and the difficulty of escape of capsules, ease of rupture of capsules, ease of leakage of enclosed matter during application, smoothness during application and skin wetness when the respective samples were applied onto the skin on the innerside of the forearm were represented by an overall evaluation, by an organoleptic test, by a panel of 10.

The evaluation was divided into the following 4 rankings:
⊚: very good

○: good
△: average
x: poor

The breaking strength of the microcapsules taken out of the gel-like cosmetic was measured at the same time.

| | |
|---|---|
| Squalane | 5.0 parts |
| Petrolatum | 2.0 |
| Beeswax | 0.5 |
| Sorbitane sesquioleic acid ester | 0.8 |
| Polyoxyethylene (20 mol) oleyl ether | 1.2 |
| Flavor | 0.5 |
| Preservative | q.s. |
| Microcapsule dispersion | 20.0 |
| Ethanol | 5.0 |
| Carboxyvinyl polymer (1.0% aqueous solution) | 20.0 |
| Potassium hydroxide | 0.1 |
| purified water | balance |

The breaking strength of the microcapsules taken out of the emollient lotion was measured at the same time.

TABLE 5-2

| | | | | | | | |
|---|---|---|---|---|---|---|---|
| Propylene glycol | 0 | 10 | 20 | 30 | 40 | 60 | 80 |
| Water | 100 | 90 | 80 | 70 | 60 | 40 | 20 |
| Difficulty of escape of capsules | x | x | △ | ⊚ | ⊚ | ⊚ | ⊚ |
| Ease of rupture of capsules | x | x | ○ | ⊚ | ⊚ | ⊚ | ⊚ |
| Ease of leakage of enclosed matter during application* | x | x | ○ | ⊚ | ⊚ | ⊚ | ⊚ |
| Smoothness during application (no foreign matter feeling) | x | x | △ | ⊚ | ⊚ | ⊚ | ⊚ |
| Skin wetness | x | x | ○ | ○ | ○ | ○ | ○ |
| Breaking strength of capsules (g/cm$^2$) | 1020 | 602 | 334 | 178 | 108 | 43 | 27 |

*judged as more readily leaked out, since the value (leaked amount of enclosed matter/enclosed matter formulated) is nearer to 1.

As shown in Table 5-2, the capsules having a breaking strength within the range of 10 to 300 g/cm$^2$ were found to be excellent in all the items, compared with other capsules.

EXAMPLE 5-3

Cream

Microcapsules (average particle size 58 μm) enclosing oil components at a ratio of liquid paraffin : vitamin A palmitate=92:8 prepared according to the same method as in Example 5-1, but changing the stirring speed by a homomixer to 1150 rpm, were dispersed to a weight ratio of 40% in a solution with a composition of propylene glycol : glycerine : water=50:20:30, and formulated according to the following recipe to obtain a cream.

The breaking strength of the microcapsules taken out of the cream was found to be 112 g/cm$^2$.

| | |
|---|---|
| Beeswax | 2.0 parts |
| Stearyl alcohol | 5.0 |
| Stearic acid | 8.0 |
| Squalane | 10.0 |
| Self-emulsification type propylene glycol monostearate | 3.0 |
| Polyoxyethylene cetyl ether (20 EO) | 1.0 |
| Preservative, antioxidant | q.s. |
| Triethanolamine | 1.0 |
| Microcapsule dispersion | 20.0 |
| Polyethylene glycol | 0.6 |
| Purified water | balance |

EXAMPLE 5-4

Shampoo

Microcapsules (average particle size 92 μm) enclosing oil components at a ratio of dimethylpolysiloxane : liquid paraffin=60:40 (weight ratio) prepared according to the same method as in Example 5-1, but changing the stirring speed by a homomixer to 800 rpm, were dispersed to 25% in a solution with a composition of 1,3-butylene glycol : water=40:60, and formulated according to the following recipe to obtain a shampoo.

The breaking strength of the microcapsules taken out from the shampoo was found to be 253 g/cm$^2$.

| | |
|---|---|
| AES-Na | 16.0 parts |
| Lauric acid diethanolamide | 4.0 |
| Microcapsule dispersion | 12.0 |
| Preservative, dye, flavor | q.s. |
| Purified water | balance |

EXAMPLE 5-5

Rinse

Microcapsules (average particle size 63 μm) enclosing oil components at a ratio of squalane : vitamin E=95:5 (weight ratio) prepared according to the same method as in Example 1, but changing the stirring speed by a homomixer to 1050 rpm, were dispersed to 40% in a solution with a composition of propylene glycol : polyethylene glycol : water=45:5:50, and formulated according to the following recipe to obtain a rinse.

The breaking strength of the microcapsules taken out of the rinse was found to be 211 g/cm$^2$.

| | |
|---|---|
| Stearyl trimethyl ammonium chloride | 2.0 parts |
| Cetostearyl alcohol | 3.0 |
| Glyceryl monostearate | 1.5 |
| Sodium chloride | 0.2 |
| Microcapsule dispersion | 18.0 |
| Purified water | balance |

EXAMPLE 5-6

Microcapsules (average particle size 80 μm) enclosing oil components at a ratio of liquid paraffin : vitamin C stearate=96:4 (weight ratio) prepared according to the same method as in Example 1, but changing the stirring speed by a homomixer to 920 rpm, were dispersed to 15% in a solution with a composition of glycerine : sucrose : water=70:5:25, and formulated according to the following recipe to obtain a hair cream oil.

The breaking strength of the microcapsules taken out of the hair cream oil was found to be 62 g/cm$^2$.

| | |
|---|---|
| Liquid paraffin | 30.0 parts |
| Microcrystalline wax | 3.0 |
| Polyoxyethylene (8 mol) polyoxypropylene (8 mol) 2-octyldodecyl ether | 5.0 |
| Butyl benzoate | 0.1 |
| Flavor | 0.1 |
| Oil component enclosing microcapsules | 15.0 |
| Purified water | balance |

The cosmetics formulated with the microcapsules as prepared above were evaluated.

The samples used for evaluation were the respective samples of Examples 5-3–5-6 and the following Comparative Examples 5-1–5-4.

The evaluation method was based on the difficulty of escape of capsules, ease of rupture of capsules, ease of leakage of enclosed matter during application, smoothness during application and skin wetness when the respective samples were applied onto the skin on the innerside of the forearm by an overall evaluation, by an organoleptic test, by a panel of 10.

The evaluation was divided into 4 rankings:
⊚: very good
○: good
Δ: average
x: poor

COMPARATIVE EXAMPLE 5-1

A formulation of the cream recipe was obtained by replacing propylene glycol and glycerine with an equal amount of water in the solution for dispersion of the microcapsules in Example 5-3. (The breaking strength of the microcapsules taken out of the cream was 1113 g/cm$^2$.)

COMPARATIVE EXAMPLE 5-2

A formulation of a shampoo recipe was obtained by changing the composition for dispersing the microcapsules in Example 5-4 to 1,3-butylene glycol : water=25:75. (The breaking strength of the microcapsules taken out from the shampoo was 498 g/cm$^2$.)

COMPARATIVE EXAMPLE 5-3

A formulation of a rinse recipe was obtained by changing the composition of the solution for dispersing the microcapsules in Example 5-5 to propylene glycol : polyethylene glycol : water=20:5:75. (The breaking strength of the microcapsules taken out from the rinse was 536 g/cm$^2$.)

COMPARATIVE EXAMPLE 5-4

A formulation of a foundation recipe was obtained by replacing glycerine and sucrose in the solution for dispersing the microcapsules in Example 5-6 with the equal amount of water. (The breaking strength of the microcapsules taken out from the foundation was 1046 g/cm$^2$.)

TABLE 5-3

|  | Example | | | | Comparative Example | | | |
|---|---|---|---|---|---|---|---|---|
|  | 5-3 | 5-4 | 5-5 | 5-6 | 5-1 | 5-2 | 5-3 | 5-4 |
| Difficulty of escape of capsules | ⊚ | ○ | ⊚ | ⊚ | x | x | x | x |
| Ease of rupture of capsules | ⊚ | ⊚ | ⊚ | ⊚ | x | Δ | Δ | x |
| Ease of leakage of enclosed matter during application* | ⊚ | ⊚ | ⊚ | ⊚ | x | x | x | x |
| Smoothness during application (no foreign matter feeling) | ⊚ | ○ | ⊚ | ⊚ | x | x | x | x |

*judged as more readily leaked out, since the value (leaked amount of enclosed matter/enclosed matter formulated) is nearer to 1.

As apparent from Table 5-3, the cosmetics formulated with the capsules controlled to a breaking strength of 10 to 300 g/cm$^2$ by mixing microcapsules and polyhydric alcohol were found to be more excellent in all of the items, compared with other capsules.

EXAMPLE 6-1

To a solution of 10 g of acid-treated gelatin and 10 g of gum arabic dissolved in 200 g of purified water of 60° C. was added 150 g of squalane, and the mixture was stirred by a propeller stirring machine at 600 rpm. Further, 10% aqueous acetic acid was added dropwise to the dispersion to adjust the pH to 4.3, followed by dilution with an addition of 600 g of purified water of 40° C. Subsequently, cooling was effected externally of the vessel while stirring, and 10 g of 25% aqueous glutaraldehyde was added at a liquid temperature of 8° C. and the mixture was stirred for 2 hours to harden the capsule film.

The product thus obtained was separated from the aqueous phase by decantation, and water washing was repeated, and thereafter, excess water was removed by screening to obtain capsules with an average particle size of 300 μm.

After the microcapsules were dispersed to 10% in terms of weight ratio in solutions with seven kinds of compositions of glycerine : water=0:100, 10:90, 20:80, 30:70, 40:60, 60:40, 80:20, and then formulated according to the recipes shown below to prepare cosmetic waters, and the breakage by stirring during preparation and feeling of foreign matter when applied onto the skin were evaluated, by comparison. Also, microcapsules were taken out of the cosmetic water and the breaking strength thereof measured.

| Microcapsule dispersion | 20.0 parts |
|---|---|
| Oleyl alcohol | 4.0 |
| Polyoxyethylene (20 mol) sorbitane monolauric acid ester | 1.5 |
| Polyoxyethylene (20 mol) lauryl ether | 0.5 |
| Ethanol | 10.0 |
| Flavor | 0.1 |
| Preservative | q.s. |
| Purified water | balance |

The respective experiments were conducted according to the following methods.

Evaluation of breakage during cosmetic water preparation

The breakage of capsules in the cosmetic water prepared according to the above recipe was observed by an optical microscope.

The evaluation was divided into three rankings:
○: no breakage observed
Δ: slight breakage observed
x: all capsules broken

Evaluation of feeling of foreign matter upon application to skin

The cosmetic waters formulated with the respective capsules were evaluated in the same manner as mentioned above.

Take-out of capsules

As mentioned above.

Method for measuring breaking strength

As mentioned above.

TABLE 6-1

| Glycerine | 0 | 10 | 20 | 30 | 40 | 60 | 80 |
|---|---|---|---|---|---|---|---|
| Water | 100 | 90 | 80 | 70 | 60 | 40 | 20 |
| Capsule breakage during preparation | o | o | o | o | o | o | o |
| Foreign matter feeling during application to skin | x | x | o | o | o | o | o |
| Breaking strength of capsules (g/cm$^2$) | 984 | 509 | 281 | 158 | 92 | 41 | 18 |

As shown in Table 6-1, the microcapsules having a breaking strength in the range of 10 to 300 g/cm$^2$ were found to be excellent in all of the items, compared with other microcapsules.

EXAMPLE 6-2

Microcapsules enclosing a liquid paraffin with an average particle size of 200 μm were prepared according to the same method as in Example 6-1, except that the stirrer was replaced by a homomixer and the stirring speed changed to 650 rpm.

The microcapsules were dispersed to 15% in terms of weight ratio in solutions with 7 kinds of compositions of propylene glycol : water=0:100, 10:90, 20:80, 30:70, 40:60, 60:40, 80:20, and then formulated according to the recipe shown below to prepare emollient lotions, and the difficulty of escape of capsules, ease of rupture of capsules, ease of leakage of enclosed matter during application, smoothness during application and skin wetness when the respective samples were applied to the skin on the innerside of the forearm were represented by an overall evaluation, by an organoleptic test, by a panel of 10.

The evaluation was divided into 4 rankings:
⊙: very good
○: good
Δ: average
x: poor The breaking strength of the microcapsules taken out of the gel-like cosmetic water was measured at the same time.

| Squalane | 5.0 parts |
|---|---|
| Petrolatum | 2.0 |
| Beeswax | 0.5 |
| Sorbitane sesquioleic acid ester | 0.8 |
| Polyoxyethylene (20 mol) oleyl ether | 1.2 |
| Flavor | 0.5 |
| Preservative | q.s. |
| Microcapsule dispersion | 20.0 |
| Ethanol | 5.0 |
| Purified water | balance |

The breaking strength of the microcapsules taken out of the emollient lotion was also measured at the same time.

TABLE 6-2

| Propylene glycol | 0 | 10 | 20 | 30 | 40 | 60 | 80 |
|---|---|---|---|---|---|---|---|
| Water | 100 | 90 | 80 | 70 | 60 | 40 | 20 |
| Difficulty of escape of capsules | x | x | Δ | ⊙ | ⊙ | ⊙ | ⊙ |
| Ease of rupture of capsules | x | x | o | ⊙ | ⊙ | ⊙ | ⊙ |
| Ease of leakage of enclosed matter during application* | x | x | o | ⊙ | ⊙ | ⊙ | ⊙ |
| Smoothness during application (no foreign matter feeling) | x | x | Δ | ⊙ | ⊙ | ⊙ | ⊙ |
| Skin wetness | x | x | o | ⊙ | ⊙ | ⊙ | ⊙ |
| Breaking strength of capsules (g/cm$^2$) | 980 | 551 | 328 | 166 | 98 | 44 | 23 |

*judged as more readily leaked out, since the value (leaked amount of enclosed matter/enclosed matter formulated) is nearer to 1.

As shown in Table 6-2, the capsules having a breaking strength within the range of 10 to 300 g/cm$^2$ were found to be excellent in all items, compared with other capsules.

EXAMPLE 6-3

Cream

Microcapsules (average particle size 700 μm) enclosing oil components at a ratio of liquid paraffin : vitamin A palmitate=92:8 prepared according to the same method as in Example 1, but changing the stirring speed by a homomixer to 350 rpm, were dispersed to a weight ratio of 40% in a solution with a composition of propylene glycol : glycerine : water=50:20:30, and formulated according to the following recipe to obtain a cream.

The breaking strength of the microcapsules taken out from the cream was found to be 43 g/cm$^2$.

| Beeswax | 2.0 parts |
|---|---|
| Stearyl alcohol | 5.0 |
| Stearic acid | 8.0 |
| Squalane | 10.0 |
| Self-emulsification type propylene glycol monostearate | 3.0 |
| Polyoxyethylene cetyl ether (20 EO) | 1.0 |
| Preservative, antioxidant | q.s. |
| Triethanolamine | 1.0 |
| Microcapsule dispersion | 20.0 |
| Polyethylene glycol | 0.6 |
| Purified water | balance |

EXAMPLE 6-4

Shampoo

Microcapsules (average particle size 500 μm) enclosing oil components at a ratio of dimethylpolysiloxane : liquid paraffin=60:40 (weight ratio) prepared according to the same method as in Example 6-1, but changing the stirring speed by a homomixer to 450 rpm, were dispersed to 25% in a solution with a composition of 1,3-butylene glycol : water=40:60, and formulated according to the following recipe to obtain a shampoo.

The breaking strength of the microcapsules taken out from the shampoo was found to be 208 g/cm$^2$.

| AES-Na | 16.0 parts |
|---|---|
| Lauric acid diethanolamide | 4.0 |
| Microcapsule dispersion | 18.0 |
| Preservative, dye, flavor | q.s. |
| Purified water | balance |

EXAMPLE 6-5

Rinse

Microcapsules (average particle size 400 μm) enclosing oil components at a ratio of squalane : vitamin E=95:5 (weight ratio) prepared according to the same method as in Example 6-1, but changing the stirring speed by a homomixer to 500 rpm, were dispersed to 40% in a solution with a composition of propylene glycol : polyethylene glycol : water=45:5:50, and formulated according to the following recipe to obtain a rinse.

The breaking strength of the microcapsules taken out from the rinse was found to be 142 g/cm².

| Stearyl trimethyl ammonium chloride | 2.0 parts |
|---|---|
| Cetostearyl alcohol | 3.0 |
| Glyceryl monostearate | 1.5 |
| Sodium chloride | 0.2 |
| Microcapsule dispersion | 18.0 |
| Purified water | balance |

EXAMPLE 6-6

Microcapsules (average particle size 850 μm) enclosing oil components at a ratio of fluid paraffin : vitamin C stearate=96:4 (weight ratio) prepared according to the same method as in Example 6-1, but changing the stirring speed by a homomixer to 250 rpm, were dispersed to 15% in a solution with a composition of glycerine : sucrose : water=70:5:25, and formulated according to the following recipe to obtain a hair cream oil.

The breaking strength of the microcapsules taken out of the hair cream oil was found to be 23 g/cm².

| Liquid paraffin | 30.0 parts |
|---|---|
| Microcrystalline wax | 3.0 |
| Polyoxyethylene (8 mol) polyoxypropylene (8 mol) 2-octyldodecyl ether | 5.0 |
| Butyl benzoate | 0.1 |
| Flavor | 0.1 |
| Oil component enclosing microcapsules | 15.0 |
| Purified water | balance |

The cosmetics formulated with the microcapsules as prepared above were evaluated.

The samples used for evaluation were the respective samples of Examples 6-3 to 6-6 and the following Comparative Examples 6-1 to 6-4.

The evaluation method was based on the difficulty of escape of capsules, ease of rupture of capsules, ease of leakage of enclosed matter during application, smoothness during application and skin wetness when the respective samples were applied to the skin on the innerside of forearm an overall evaluation, by an organoleptic test, by a panel of 10.

The evaluation was divided into 4 rankings:
⊚: very good
◯: good
Δ: average
x: poor

COMPARATIVE EXAMPLE 6-1

A formulation of a cream recipe was obtained by replacing propylene glycol and glycerine with the equal amount of water in the solution for dispersion of the microcapsules in Example 6-3. (The breaking strength of the microcapsules taken out from the cream was 502 g/cm².)

COMPARATIVE EXAMPLE 6-2

A formulation of a shampoo recipe was obtained by changing the composition for dispersing the microcapsules in Example 6-4 to 1,3-butylene glycol : water=25:75. (The breaking strength of the microcapsules taken out from the shampoo was 483 g/cm².)

COMPARATIVE EXAMPLE 6-3

A formulation of a rinse recipe was obtained by changing the composition of the solution for dispersing the microcapsules in Example 6-5 to propylene glycol : polyethylene glycol : water=20:5:75. (The breaking strength of the microcapsules taken out from the rinse was 345 g/cm².)

COMPARATIVE EXAMPLE 6-4

A formulation of a foundation recipe was obtained by replacing glycerine and sucrose in the solution for dispersing the microcapsules in Example 6-6 with the equal amount of water. (The breaking strength of the microcapsules taken out from the foundation was 418 g/cm².)

TABLE 6-3

| | Example | | | | Comparative Example | | | |
|---|---|---|---|---|---|---|---|---|
| | 6-3 | 6-4 | 6-5 | 6-6 | 6-1 | 6-2 | 6-3 | 6-4 |
| Difficulty of escape of capsules | ⊚ | ⊚ | ⊚ | ⊚ | X | X | X | X |
| Ease of rupture of capsules | ⊚ | ⊚ | ⊚ | ⊚ | X | X | Δ | X |
| Ease of leakage of enclosed matter during application* | ⊚ | ⊚ | ⊚ | ⊚ | X | X | X | X |
| Smoothness during application (no foreign matter feeling) | ⊚ | ⊚ | ⊚ | ⊚ | X | X | X | X |

*judged as more readily leaked out since the value (leaked amount of enclosed matter/enclosed matter formulated) is nearer to 1.

As apparent from Table 6-3, the cosmetics formulated with the capsules controlled to a breaking strength of 10 to 300 g/cm² by mixing microcapsules and polyhydric alcohol were found to be more excellent in all of the items, compared with other microcapsules.

EXAMPLE 7-1

With 600 g of an aqueous solution of 40° C. containing 10 g of acid-treated gelatin dissolved therein was mixed 600 g of an aqueous solution of 40° C. containing 10 g of gum arabic dissolved therein, and the pH was adjusted to 4.3 by dropwise adding 10% aqueous acetic acid, and then 150 g of water-in-oil type emulsion (W/O type emulsion) prepared according to the following recipe was added, followed by stirring at 400 rpm by a propeller stirring machine. Subsequently, cooling was effected externally of the vessel while stirring, and 10 g of aqueous 25% glutaraldehyde solution was added at a liquid temperature of 8° C., followed by stirring for 2 hours to harden the capsule film.

The product thus obtained was separated from the aqueous phase by decantation, and by repeated water washing, capsules with an average particle size of 500 μm with a weight ratio of gelating film and the W/O type emulsion enclosed of 1:60 were obtained.

| Oil Phase | |
|---|---|
| Squalane | 21.0 (part) |
| Vitamin A palmitate | 2.0 |
| Cyclic silicone | 5.0 |
| Organic modified clay mineral obtained by treating 0.5 g of bentone-38 with 0.1 g of dimyristoyl lecithin | 0.6 |
| Microcrystalline wax | 2.0 |
| Butyl parahydroxybenzoate | 0.1 |
| Aqueous Phase | |
| L-ascorbic acid | 2.0 |

| | |
|---|---|
| Dipropylene glycol | 5.0 |
| Purified water | balance |

Preparation method: While stirring the aqueous phase portion dissolved at 70° C. with a disper, the oil phase dispersed by mixing at 70° C. was gradually added to be emulsified, followed by cooling.

The capsules were formulated according to the following recipe to prepare an O/W type emollient lotion.

| | |
|---|---|
| Oil Phase | |
| Squalane | 5.0 (part) |
| Petrolatum | 2.0 |
| Beeswax | 0.5 |
| Sorbitan sesquioleic acid ester | 0.8 |
| Polyoxyethylene (20 mole) oleyl ether | 1.2 |
| Flavor | 0.5 |
| Preservative | q.s. |
| Aqueous Phase | |
| Microcapsules enclosing W/O type emulsion | 10.0 |
| Propylene glycol | 5.0 |
| Ethanol | 5.0 |
| Carboxyvinyl polymer (1.0% aqueous solution) | 20.0 |
| Potassium hydroxide | 0.1 |
| Purified water | balance |

Also, as a Comparative Example, an emollient lotion having the same amounts of squalane and vitamin A palmitate as the enclosed amounts in the oil phase and L-ascorbic acid in the aqueous phase without formulation of microcapsules in the above recipe (Comparative Example 7-1) was prepared, and a comparative evaluation with the above Example was conducted of the stability with a lapse of time of the vitamin A palmitate and L-ascorbic acid.

The experiments were conducted by storing the vessels containing the respective emollient lotions in a thermostat at 50° C., and the amounts of vitamin A palmitate and L-ascorbic acid remaining after 7, 14, 30, and 60 days were determined.

Figure 2:
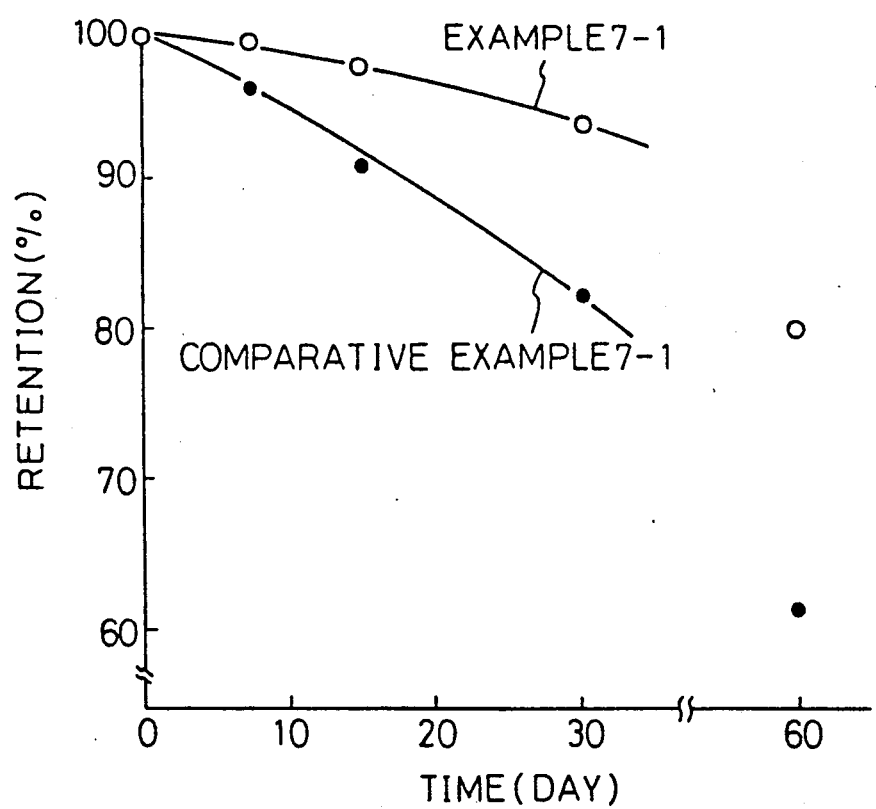
FIG. 2 is a graph showing the stability with a lapse of time of the vitamin A palmitate of Example 7-1 and Comparative Example 7-1.
Figure 3:
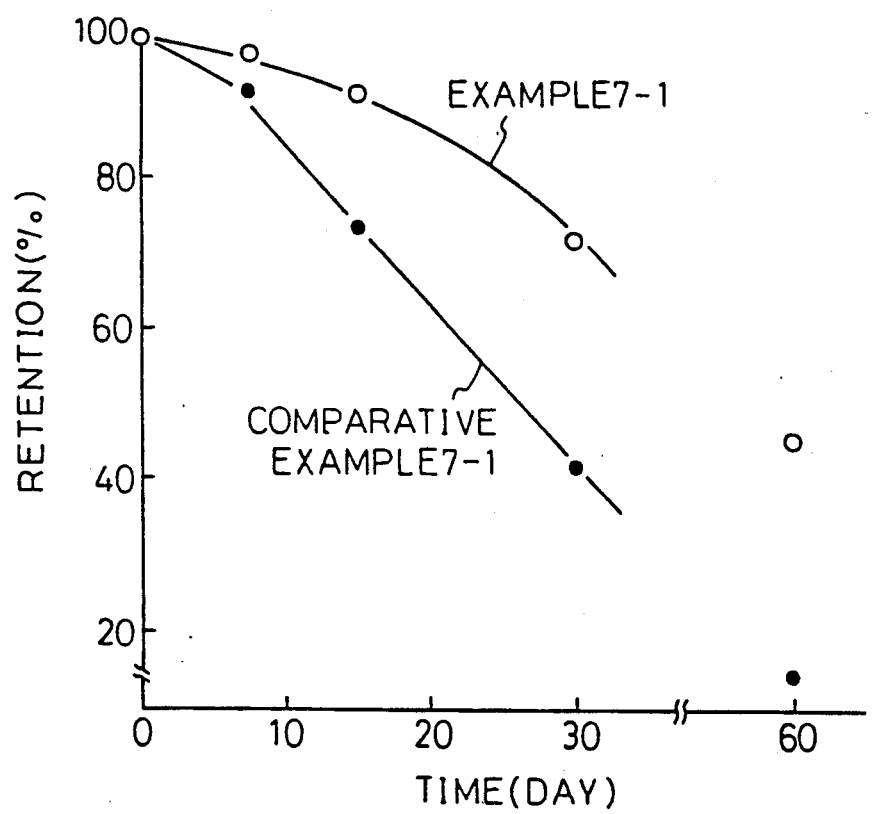
FIG. 3 is a graph showing the stability with a lapse of time of the L-ascorbic acid of Example 7-1 and Comparative Example 7-1.

The results are shown in FIG. 2 and FIG. 3. In each figure, the amount immediately after preparation of the emollient lotion is represented as 100%. Example 7-1 shows a slower reduction of vitamin A palmitate and L-ascorbic acid with a lapse of time, and thus shows an excellent in stability.

EXAMPLE 7-2

With 600 g of an aqueous solution of 50° C. containing 10 g of acid-treated gelatin dissolved therein was mixed 600 g of an aqueous solution of 50° C. containing 8 g of gum arabic dissolved therein, and the pH was adjusted to 4.5 by dropwise adding 10% aqueous acetic acid, and then 100 g of W/O type emulsion prepared according to the following recipe was added, followed by stirring at 1000 rpm by a propeller stirring machine. Subsequently, cooling was effected externally of the vessel while stirring, and 10 g of aqueous 25% glutaraldehyde solution was added at a liquid temperature of 10° C., followed by stirring for 2 hours to harden the capsule film.

The product thus obtained was separated from the aqueous phase by decantation, and by repeated water washing, capsules with an average particle size of 50 μm with a weight ratio of gelating film and the W/O type emulsion enclosed of 1:20 were obtained.

| | |
|---|---|
| Oil Phase | |
| Squalane | 25.0 (part) |
| Ceresine | 3.0 |
| Microcrystalline wax | 1.5 |
| Lanolin | 0.5 |
| Petrolatum | 6.0 |
| γ-linoleinic acid | 0.5 |
| Amino Acid W/O Gel | |
| Glycerine monooleate | 4.0 |
| Monosodium L-glutamate | 3.2 |
| Purified water | 12.8 |
| Aqueous Phase | |
| Vitamin B$_6$ hydrochloride | 0.4 |
| Propylene glycol | 5.0 |
| Purified water | balance |

Preparation method: To purified water heated to 70° C. was added monosodium L-glutamate to be dissolved therein, and the solution was added to glycerine monooleate of 70° C. to prepare an amino acid W/O gel by a homomixer, and then the oil phase portion and the aqueous phase portion dissolved by heating to 70° C. were added and emulsified homogeneously by a homomixer, followed by cooling by a heat-exchanger.

The capsules were formulated according to the following recipe to prepare a W/O type hair oil cream.

| | |
|---|---|
| Oil Phase | |
| Liquid paraffin | 30.0 (part) |
| Microcrystalline wax | 3.0 |
| Polyoxyethylene (8 mole) polyoxypropylene (8 mole) 2-octyldodecyl ether | 5.0 |
| Butyl benzoate | 0.1 |
| Flavor | 0.1 |
| Aqueous Phase | |
| Microcapsules enclosing W/O type emulsion | 15.0 |
| Purified water | balance |

Also, as a Comparative Example, a hair cream oil having the same amount of γ-linolenic acid as the enclosed amount in the oil phase and vitamin B$_6$ hydrochloride in the aqueous phase without formulation of the microcapsules in the above recipe (Comparative Example 7-2) was prepared, and a comparative evaluation with the above Example was conducted of the stability with a lapse of time of the γ-linolenic acid and vitamin B$_6$ hydrochloride, according to the same experimental method as in Example 7-1.

Figure 4:
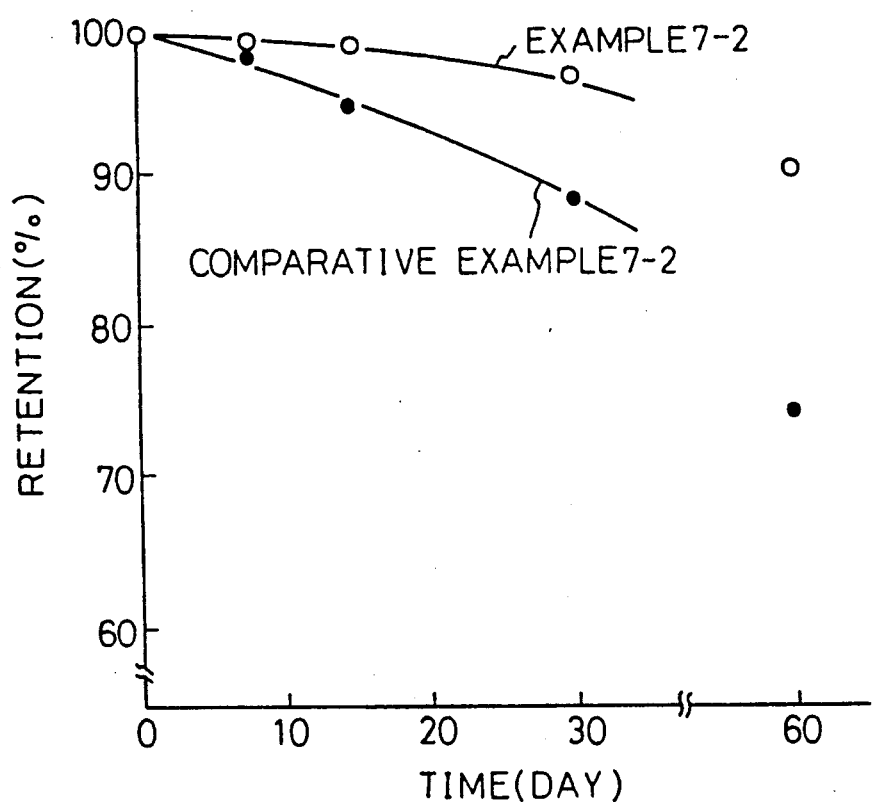
FIG. 4 is a graph showing the stability with a lapse of time of γ-linolenic acid of Example 7-2 and Comparative Example 7-2.
Figure 5:
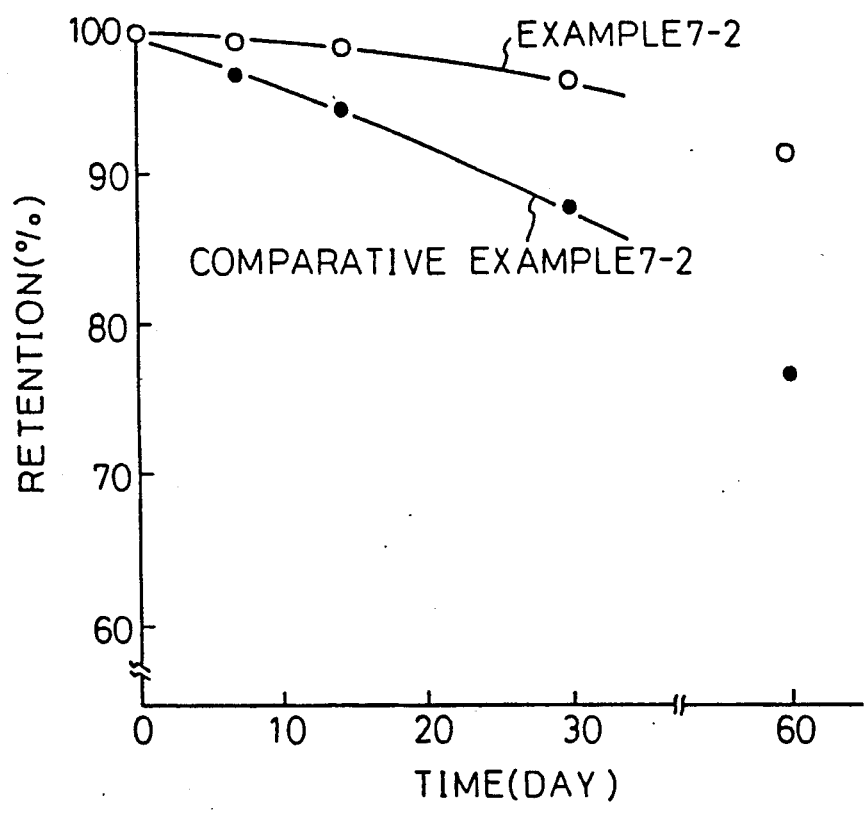
FIG. 5 is a graph showing the stability with a lapse of time of the vitamin $B_6$ hydrochloride of Example 7-2 and Comparative Example 7-2; and, FIG. 6 is a graph showing the leakage characteristics of a cream base with a lapse of time of the L-ascorbic acid of Example 7-3 and Comparative Example 7-3.

The results are shown in FIG. 4 and FIG. 5, from which it can be seen that Example 7-2 was found to have excellent stability of both components, compared with Comparative Example 7-2.

EXAMPLE 7-3

The W/O type emulsion enclosing microcapsules prepared in Example 7-1 were formulated according to the following recipe to obtain a cream.

| | |
|---|---|
| Oil Phase | |
| Squalane | 5.0 (part) |
| Reduced lanolin | 2.0 |
| Stearic acid | 2.0 |
| Stearyl alcohol | 7.0 |
| Octyldodecanol | 6.0 |
| Polyoxyethylene (25 mole) cetyl ether | 3.0 |

| -continued | |
|---|---|
| Lipophilic type glycerine monostearate | 2.0 |
| Flavor | 0.3 |
| Preservative | q.s. |
| Aqueous Phase | |
| Microcapsules | 10.0 |
| Propylene glycol | 5.0 |
| Purified water | balance |

The cream was left to stand at room temperature for 10, 30, 60, 120, 180, and 360 days, and the amount of L-ascorbic acid migrated (leaked out) to the outer phase (cream base) of microcapsules was determined. The experiment method was conducted by separating each sample after a lapse of time into the cream base layer and the microcapsule layer by centrifugation at 5000 rpm (with the microcapsule being the upper layer), and quantitatively determining the L-ascorbic acid contained in the cream base. As a Comparative Example, the same investigations were made for the microcapsules of nylon film enclosing L-ascorbic acid (Comparative Example 7-3). The microcapsules of nylon film were prepared by an interfacial polymerization of ethylenediamine and terephthalic acid chloride, as generally practiced in the art.

Figure 6:
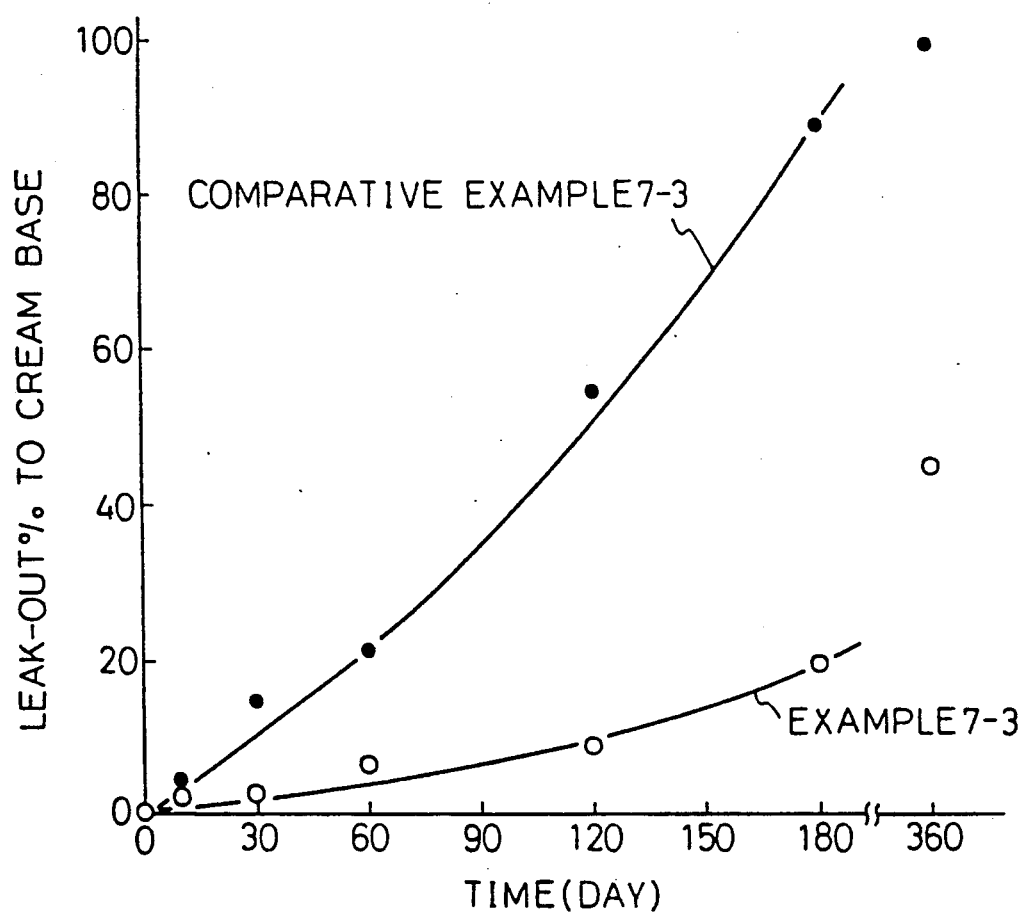

The results are shown in FIG. 6, from which it can be seen that Example has a low level of leakage of L-ascorbic acid from the microcapsule for a long term, compared with the Comparative Example.

EXAMPLE 7-4

Foundation

Microcapsules with an average particle size of 20 μm were prepared according to the same method as in Example 7-1 enclosing the W/O type emulsion of the following recipe, with a propeller at a stirring speed of 1200 rpm.

| Oil Phase Portion | |
|---|---|
| Microcrystalline wax | 9.0 (part) |
| Paraffin | 2.0 |
| Beeswax | 3.0 |
| Petrolatum | 5.0 |
| Reduced lanolin | 8.0 |
| Squalane | 24.0 |
| Isopropyl myristate | 10.0 |
| Pyridoxin dicaprylate | 0.5 |
| Hexadecylazipic acid ester | 10.0 |
| Lipophilic glycerine monooleate | 3.5 |
| Polyoxyethylene (20 mole) sorbitan monooleic acid ester | 1.0 |
| Preservative | q.s. |
| Aqueous Phase Portion | |
| Dipotassium glycylrithinate | 0.5 |
| Propylene glycol | 2.0 |
| Purified water | balance |

Preparation method: The aqueous phase portion heated to 70° C. was added to the oil phase portion dissolved by heating at 70° C. to effect preliminary emulsification, and then homogeneously emulsified by a homomixer, followed by cooling to 30° C. by a heat-exchanger.

The capsules were formulated according to the following recipe to obtain a foundation.

| Talc | 20.0 (part) |
|---|---|
| Titanium dioxide | 8.0 |
| Kaolin | 7.0 |

| -continued | |
|---|---|
| Solid paraffin | 5.0 |
| Lanolin | 10.0 |
| Fluid paraffin | 27.0 |
| Sorbitan sesquioleic acid ester | 5.0 |
| Pigment | q.s. |
| Flavor | q.s. |
| Preservative | q.s. |
| Microcapsules enclosing W/O type emulsion | 5.0 |
| Purified water | balance |

The present foundation, because of containing water by the W/O type emulsion enclosed within the microcapsules, had a usability not found in the prior art, and because the lipid-soluble and water-soluble effective components are stably maintained, was found to be extremely excellent in maintaining constant characteristics of skin.

EXAMPLE 8-1

Into 400 g of an aqueous gelatin solution of 40° C. containing 10 g of acid-treated gelatin dissolved therein was added 400 g of an aqueous solution of 40° C. containing 10 g of gum arabic dissolved therein, and further, an aqueous 10% acetic acid was added to adjust pH to 4.3 to form a complex coacervate, and thereafter, 4 kinds of oil components of 40 g of squalane colored red with Sudan III, 40 g of liquid paraffin colored yellow with Quinoline Yellow SS, 40 g of jojoba oil colored blue with Quinizalin Green and 10 g of noncolored vitamin A palmitate were successively added into the coacervation aqueous solution as described above, and the mixture was stirred by a propeller stirring machine at 300 rpm. Next, cooling was effected externally of the vessel while stirring, and 10 g of an aqueous 25% glutaraldehyde was added at a liquid temperature of 8° C., followed by stirring for 2 hours to harden the capsule film.

The product thus obtained was separated from the aqueous phase by decantation, and by repeated water washing, four kinds of microcapsules, red, yellow, blue and colorless, with no mutually mixing between oils and an average particle size of 500 μm, were obtained.

For comparison, microcapsules were produced according to the method in which, after a successive addition of the four kinds of oils into the aqueous gelatin solution, complex coacervation was caused by an addition of an aqueous gum arabic solution. As a result, oils were mutually mixed with each other to give only black microcapsules in which the red, yellow and blue colors were mixed.

EXAMPLE 8-2

After 200 g of an aqueous gelatin solution of 40° C. containing 10 g of acid-treated gelatin dissolved therein was adjusted to a pH of 7 with 10% acetic acid and 10% sodium hydroxide and 64 g of ethanol added to form a simple coacervate, 4 kinds of oil components of 10 g of squalane colored red with aluminum lake of Acid Red, 10 g of fluid paraffin colored yellow with aluminum lake of Sunset Yellow, 10 g of jojoba oil colored blue with aluminum lake of Brilliant Blue, and 5 g of noncolored vitamin A palmitate were added successively to the coacervation aqueous solution as described above, followed by stirring by a propeller stirring machine at 500 rpm. Next, cooling was effected externally of the vessel while stirring, and 20 g of a 10% aqueous solution of potassium alum was added at a liquid temperature of 5° C. and stirring was conducted for 2 hours to harden the capsule film.

The product thus obtained was separated from the aqueous phase by decantation, and by repeated water washing, four kinds of microcapsules, red, yellow, blue, and colorless, in which oils were not mixed mutually with each other, and having an average particle size of 200 μm were obtained.

For comparison, microcapsules were produced according to the method in which, after a successive addition of the four kinds of the oils into the aqueous gelatin solution, ethanol was added to cause a simple coacervation. As a result, the oils were mutually mixed with each other to give only black microcapsules in which the red, yellow and blue colors were mixed with each other.

EXAMPLE 8-3

After 22 g of a 20% aqueous sodium sulfate solution was added to 100 g of an aqueous solution of 60° C. containing 2 g of cellulose acetate phthalate dissolved therein to form a simple coacervate, four kinds of 5 g of cetyl isooleate colored orange with aluminum lake of Orange II, 5 g of cottonseed oil colored yellow with aluminum lake of Tartrazine, 5 g of macademia nut oil colored purple with aluminum lake of Arizrose Purple, and 1 g of non-colored linoleic acid were successively added to the coacervation aqueous solution as described above, followed by stirring by a propeller stirring machine at 800 rpm. Next, cooling was effected externally of the vessel, while stirring, to make the liquid temperature 5° C. The product thus obtained was separated from the aqueous phase by decantation, and thereafter, washing was repeated with 5% aqueous sodium sulfate solution and the capsule film was hardened with 2% aqueous acetic acid, whereby four kinds of microcapsules, orange, yellow, purple, and colorless, in which oils were not mixed mutually with each other and all having an average particle size of 100 μm, were obtained.

For comparison, microcapsules were obtained by the method in which a simple coacervation was caused by an addition of sodium sulfate after a successive addition of the four kinds of oils into the aqueous cellulose acetate phthalate solution. As a result, the oils were mutually mixed with each other to give only black microcapsules in which the orange, yellow and purple colors are mixed with each other.

COMPARATIVE EXAMPLE 8-1

To 400 g of an aqueous gelatin solution of 60° C. containing 25 g of acid-treated gelatin dissolved therein, 50 g of an aqueous solution of 60° C. containing 2.5 g of carboxymethyl cellulose (etheration degree: 0.6, average polymerization degree: 150) dissolved therein was added, and further, an aqueous 10% acetic acid and an aqueous 10% sodium hydroxide were added to adjust pH 5.5 to form a complex coacervate. Then, 7 kinds of oil components of 10 g of ethyl linolate (Oil A), 10 g of a mixed oil of squalane : vitamin C palmitate=9:1 (Oil B), 10 g of oleic acid (Oil C), 10 g of tocopherol acetate (Oil D), 10 g of a mixed oil of neopentyl glycol didecanoate : ethylhexyl paradimethylaminobenzoate=7:3 (Oil E), 10 g of dimethylpolysiloxane (Oil F) and 10 g of vitamin A palmitate (Oil G) were successively added into the coacervation aqueous solution as described above, followed by stirring by a propeller stirring machine at 100 rpm. Next, cooling was effected while stirring and 10 g of a 25% aqueous solution was added at a liquid temperature of 8° C., followed by stirring for 2 hours to harden the capsule film.

The product thus obtained was separated from the aqueous phase by decantation, and by repeated water washing, microcapsules with an average particle size of 1000 μm were obtained.

From these microcapsules, 10 microcapsules were randomly selected, and from each the enclosed oil was taken out with a microsyringe and examined to determine whether the oils were mutually mixed during preparation, by the liquid chromatography method and the gas chromatography method. For comparison, microcapsules were produced according to the method in which complex coacervation is effected by an addition of an aqueous gum arabic solution after a successive addition of 7 kinds of oils into the aqueous gelatin solution, and examined according to the same method. The results are shown in Table 8-1. In the Examples, microcapsules in which oils were not mutually mixed with each other at all were obtained, but in all of the Comparative Examples, several kinds of oils were mutually mixed with each other during preparation of the microcapsules.

TABLE 8-1

|  | Capsule No. | Enclosed oil species analyzed |
|---|---|---|
| Example | 8-1 | Oil G |
|  | 8-2 | Oil C |
|  | 8-3 | Oil A |
|  | 8-4 | Oil B |
|  | 8-5 | Oil A |
|  | 8-6 | Oil D |
|  | 8-7 | Oil C |
|  | 8-8 | Oil G |
|  | 8-9 | Oil A |
|  | 8-10 | Oil E |
| Comparative Example | 8-1 ∫ 8-10 | Mixtures of several kinds of oils |

We claim:

1. A basic make-up or hair cosmetic composition comprising microcapsules with an average particle size of 50 to 1000 μm composed of a gelatin film swollen with water enclosing a hydrophobic cosmetic component therein, wherein a mixture of a liquid oil component and a solid oil component or a semi-solid oil component is used as the hydrophobic component, and microcapsules with a breaking strength of 10 to 300 g/cm$^2$ are formulated, wherein said liquid oil component has a melting point below room temperature and is at least one member selected from the group consisting of animal and vegetable oils, hydrocarbon oils, ester oils, silicone oils, higher fatty acids, higher alcohols, sunscreening agents, vitamins, alpha lipoic acid, ferulic acid, and flavors and said solid or semi-solid oil component is at least one member selected from the group consisting of animal and vegetable oils, hydrocarbon oils, ester oils, higher fatty acids, higher alcohols, waxes, sunscreening agents and flavors.

2. A basic make-up or hair cosmetic composition comprising microcapsules with an average particle size of 50 to 1000 μm composed of a gelatin film swollen with water enclosing a hydrophobic cosmetic component therein, wherein a mixture of a liquid oil component and a solid oil component or a semi-solid oil component is used as the hydrophobic component, and microcapsules with a breaking strength of 10 to 300 g/cm² are formulated, wherein said liquid oil component is at least one member selected from the group consisting of animal and vegetable oils, hydrocarbon oils, ester oils, silicone oils, higher fatty acids, higher alcohols, sunscreening agents, vitamins, alpha lipoic acid, ferulic acid, and flavors and said solid or semi-solid oil component is at least one member selected from the group consisting of animal and vegetable oils, hydrocarbon oils, ester oils, higher fatty acids, higher alcohols, waxes, sunscreening agents and flavors, the solid or semi-solid oil having a melting point above room temperature and being dissolved or dispersed in the liquid oil component.

* * * * *